US008871241B2

(12) United States Patent
Chou et al.

(10) Patent No.: US 8,871,241 B2
(45) Date of Patent: Oct. 28, 2014

(54) INJECTABLE SUSTAINED RELEASE DELIVERY DEVICES

(75) Inventors: Kang-Jye Chou, Watertown, MA (US); Hong Guo, Belmont, MA (US); Paul Ashton, Boston, MA (US); Robert W. Shimizu, Acton, MA (US); David A. Watson, Westwood, MA (US)

(73) Assignee: pSivida US, Inc., Watertown, MA (US)

( * ) Notice: Subject to any disclaimer, the term of this patent is extended or adjusted under 35 U.S.C. 154(b) by 1563 days.

(21) Appl. No.: 10/714,549

(22) Filed: Nov. 13, 2003

(65) Prior Publication Data

US 2004/0176341 A1   Sep. 9, 2004

Related U.S. Application Data

(63) Continuation-in-part of application No. 10/428,214, filed on May 2, 2003, now abandoned.

(60) Provisional application No. 60/452,348, filed on Mar. 6, 2003, provisional application No. 60/437,576, filed on Dec. 31, 2002, provisional application No. 60/377,974, filed on May 7, 2002, provisional application No. 60/425,943, filed on Nov. 13, 2002.

(51) Int. Cl.
| | |
|---|---|
| *A61F 2/00* | (2006.01) |
| *A61K 9/28* | (2006.01) |
| *A61K 9/00* | (2006.01) |
| *A61K 31/58* | (2006.01) |
| *A61K 45/06* | (2006.01) |
| *A61K 9/24* | (2006.01) |
| *A61K 31/7072* | (2006.01) |
| *A61K 9/20* | (2006.01) |

(52) U.S. Cl.
CPC ............. *A61K 9/0004* (2013.01); *A61K 9/2886* (2013.01); *A61K 9/2853* (2013.01); *A61K 31/58* (2013.01); *A61K 9/0051* (2013.01); *A61K 45/06* (2013.01); *A61K 9/209* (2013.01); *A61K 31/7072* (2013.01); *A61K 9/0092* (2013.01); *A61K 9/284* (2013.01); *A61K 9/2086* (2013.01); *A61K 9/204* (2013.01); *A61K 9/0024* (2013.01)
USPC ........... 424/425; 424/428; 424/426; 424/424; 424/422

(58) Field of Classification Search
USPC .......................... 424/426, 425, 424, 423, 428
See application file for complete search history.

(56) References Cited

U.S. PATENT DOCUMENTS

| | | | |
|---|---|---|---|
| 3,416,350 A | 12/1968 | Ness | |
| 3,618,604 A | 11/1971 | Ness | |
| 3,630,200 A | 12/1971 | Higuchi | |
| 3,632,739 A | 1/1972 | Kornblum | |
| 3,829,570 A | 8/1974 | Heider et al. | |
| 3,854,480 A | 12/1974 | Zaffaroni | |
| 3,896,819 A | 7/1975 | Zaffaroni et al. | |
| 3,916,899 A | 11/1975 | Theeuwes et al. | |
| 3,948,254 A | 4/1976 | Zaffaroni | |
| 3,961,628 A | 6/1976 | Arnold | |
| 3,977,404 A | 8/1976 | Theeuwes | |
| 3,980,463 A | 9/1976 | Muramoto et al. | |
| 3,993,071 A | 11/1976 | Higuchi et al. | |
| 4,008,719 A | 2/1977 | Theeuwes et al. | |
| 4,014,334 A | 3/1977 | Theeuwes et al. | |
| 4,014,335 A | 3/1977 | Arnold | |
| 4,034,758 A | 7/1977 | Theeuwes | |
| 4,036,227 A | 7/1977 | Zaffaroni et al. | |
| 4,077,407 A | 3/1978 | Theeuwes et al. | |
| 4,111,201 A | 9/1978 | Theeuwes | |
| 4,111,203 A | 9/1978 | Theeuwes | |

(Continued)

FOREIGN PATENT DOCUMENTS

| | | |
|---|---|---|
| CA | 2544460 A1 | 5/2001 |
| CN | 1200033 A | 11/1999 |

(Continued)

OTHER PUBLICATIONS

Kajihara et al., Journal of Controlled Release, 73, pp. 279-291 (2001).

(Continued)

*Primary Examiner* — Johann R Richter
*Assistant Examiner* — Danielle Sullivan
(74) *Attorney, Agent, or Firm* — David P. Halstead; Foley Hoag LLP

(57) ABSTRACT

An injectable drug delivery device includes a core containing one or more drugs and one or more polymers. The core may be surrounded by one or more polymer outer layers (referred to herein as "coatings," "skins," or "outer layers"). In certain embodiments, the device is formed by extruding or otherwise preforming a polymeric skin for a drug core. The drug core may be co-extruded with the skin, or inserted into the skin after the skin has been extruded, and possibly cured. In other embodiments, the drug core may be coated with one or more polymer coatings. These techniques may be usefully applied to fabricate devices having a wide array of drug formulations and skins that can be selected to control the release rate profile and various other properties of the drugs in the drug core in a form suitable for injection using standard or non-standard gauge needles. The device may be formed by combining at least one polymer, at least one drug, and at least one liquid solvent to form a liquid suspension or solution wherein, upon injection, such suspension or solution under goes a phase change and forms a gel. The configuration may provide for controlled release of the drug(s) for an extended period.

31 Claims, 9 Drawing Sheets

(56) References Cited

U.S. PATENT DOCUMENTS

| | | | |
|---|---|---|---|
| 4,135,514 A | 1/1979 | Zaffaroni et al. | |
| 4,142,526 A | 3/1979 | Zaffaroni et al. | |
| 4,177,256 A | 12/1979 | Michaels et al. | 424/427 |
| 4,186,184 A | 1/1980 | Zaffaroni | |
| 4,200,098 A | 4/1980 | Ayer et al. | |
| 4,247,498 A | 1/1981 | Castro | |
| 4,256,108 A | 3/1981 | Theeuwes | |
| 4,260,736 A | 4/1981 | Asano et al. | |
| 4,283,394 A | 8/1981 | West et al. | |
| 4,290,426 A | 9/1981 | Luschen et al. | |
| 4,304,232 A | 12/1981 | Michaels | |
| 4,304,765 A | 12/1981 | Shell et al. | |
| 4,322,323 A | 3/1982 | Capozza | |
| 4,326,525 A | 4/1982 | Swanson et al. | |
| 4,327,725 A | 5/1982 | Cortese et al. | |
| 4,351,337 A | 9/1982 | Sidman | |
| 4,439,196 A | 3/1984 | Higuchi | |
| 4,475,916 A | 10/1984 | Himmelstein | |
| 4,478,818 A | 10/1984 | Shell et al. | |
| 4,484,922 A | 11/1984 | Rosenwald | |
| 4,519,801 A | 5/1985 | Edgren | |
| 4,519,909 A | 5/1985 | Castro | |
| 4,522,625 A | 6/1985 | Edgren | |
| 4,609,374 A | 9/1986 | Ayer | |
| 4,615,698 A | 10/1986 | Guittard et al. | |
| 4,624,847 A | 11/1986 | Ayer et al. | |
| 4,627,850 A | 12/1986 | Deters et al. | |
| 4,652,441 A | 3/1987 | Okada et al. | |
| 4,657,543 A | 4/1987 | Langer et al. | |
| 4,673,405 A | 6/1987 | Guittard et al. | |
| 4,681,755 A | 7/1987 | Colombo et al. | |
| 4,692,336 A | 9/1987 | Eckenhoff et al. | |
| 4,693,886 A | 9/1987 | Ayer | |
| 4,711,782 A | 12/1987 | Okada et al. | |
| 4,716,031 A | 12/1987 | Eckenhoff et al. | |
| 4,717,567 A | 1/1988 | Wu et al. | |
| 4,720,384 A | 1/1988 | DiLuccio et al. | |
| 4,730,013 A | 3/1988 | Bondi et al. | |
| 4,740,365 A | 4/1988 | Yukimatsu et al. | |
| 4,743,247 A | 5/1988 | Wong | |
| 4,764,364 A * | 8/1988 | Heller et al. | 514/772.7 |
| 4,777,049 A | 10/1988 | Magruder et al. | |
| 4,786,500 A | 11/1988 | Wong | |
| 4,789,513 A | 12/1988 | Cloeren | 264/173.13 |
| 4,806,382 A | 2/1989 | Goldberg et al. | |
| 4,814,323 A | 3/1989 | Andrieu et al. | |
| 4,830,860 A | 5/1989 | Ranade | |
| 4,832,957 A | 5/1989 | Dempski et al. | |
| 4,839,177 A | 6/1989 | Colombo et al. | |
| 4,839,342 A | 6/1989 | Kaswan | |
| 4,861,627 A | 8/1989 | Mathiowitz et al. | |
| 4,863,455 A | 9/1989 | Whitehead | |
| 4,863,735 A * | 9/1989 | Kohn et al. | 424/422 |
| 4,865,846 A | 9/1989 | Kaufman | |
| 4,877,618 A | 10/1989 | Reed, Jr. | |
| 4,882,150 A | 11/1989 | Kaufman | |
| 4,889,720 A | 12/1989 | Konishi | |
| 4,891,223 A | 1/1990 | Ambegaonkar et al. | |
| 4,898,733 A | 2/1990 | DePrince et al. | |
| 4,913,906 A | 4/1990 | Friedman et al. | |
| 4,927,632 A | 5/1990 | Wong | |
| 4,927,687 A | 5/1990 | Nuwayser | |
| 4,945,089 A | 7/1990 | Clark | |
| 4,946,456 A | 8/1990 | Roth et al. | |
| 4,952,402 A | 8/1990 | Sparks et al. | |
| 4,959,217 A | 9/1990 | Sanders et al. | |
| 4,994,273 A | 2/1991 | Zentner et al. | |
| 5,028,435 A | 7/1991 | Katz et al. | |
| 5,035,891 A | 7/1991 | Runkel et al. | |
| 5,088,505 A | 2/1992 | De Nijs et al. | |
| 5,091,185 A | 2/1992 | Castillo et al. | |
| 5,098,443 A | 3/1992 | Parel et al. | |
| 5,102,389 A | 4/1992 | Hauser | |
| 5,120,548 A | 6/1992 | McClelland et al. | |
| 5,124,392 A | 6/1992 | Robertson et al. | |
| 5,141,752 A | 8/1992 | Ayer et al. | |
| 5,147,647 A | 9/1992 | Darougar | |
| 5,156,623 A | 10/1992 | Hakamatsuka et al. | |
| 5,174,999 A | 12/1992 | Magruder et al. | |
| 5,201,764 A | 4/1993 | Kelman et al. | |
| 5,213,808 A | 5/1993 | Bar-Shalom et al. | |
| 5,226,902 A | 7/1993 | Bae et al. | |
| 5,294,604 A | 3/1994 | Nussenblatt et al. | |
| 5,314,419 A | 5/1994 | Pelling | |
| 5,342,622 A | 8/1994 | Williams et al. | |
| 5,378,475 A | 1/1995 | Smith et al. | |
| 5,389,382 A | 2/1995 | List et al. | |
| 5,393,536 A | 2/1995 | Brandt et al. | 425/112 |
| 5,411,952 A | 5/1995 | Kaswan | |
| 5,413,572 A | 5/1995 | Wong et al. | |
| 5,431,921 A | 7/1995 | Thombre | |
| 5,435,998 A | 7/1995 | Abelson | |
| 5,443,505 A * | 8/1995 | Wong et al. | 623/4.1 |
| 5,474,979 A | 12/1995 | Ding et al. | |
| 5,476,511 A | 12/1995 | Gwon et al. | |
| 5,482,934 A | 1/1996 | Calatayud et al. | |
| 5,512,293 A | 4/1996 | Landrau et al. | |
| 5,543,441 A | 8/1996 | Rhee et al. | |
| 5,554,187 A | 9/1996 | Rizzo, III | |
| 5,569,429 A | 10/1996 | Luker | |
| 5,573,775 A | 11/1996 | Robertson et al. | |
| 5,593,697 A | 1/1997 | Barr et al. | |
| 5,618,560 A | 4/1997 | Bar-Shalom et al. | |
| 5,639,275 A | 6/1997 | Baetge et al. | |
| 5,650,170 A | 7/1997 | Wright et al. | |
| 5,665,373 A | 9/1997 | Robertson et al. | |
| 5,753,234 A | 5/1998 | Lee et al. | |
| 5,766,242 A | 6/1998 | Wong et al. | |
| 5,770,589 A | 6/1998 | Billson et al. | |
| 5,773,019 A | 6/1998 | Ashton et al. | |
| 5,830,546 A | 11/1998 | Ehret et al. | |
| 5,840,335 A | 11/1998 | Wenzel et al. | |
| 5,840,881 A | 11/1998 | Uda et al. | |
| 5,851,547 A | 12/1998 | Fujioka et al. | |
| 5,902,598 A | 5/1999 | Chen et al. | |
| 5,989,581 A | 11/1999 | Groenewegen | 424/433 |
| 5,998,431 A | 12/1999 | Tseng et al. | 514/300 |
| 6,039,975 A | 3/2000 | Shah et al. | |
| 6,051,576 A | 4/2000 | Ashton et al. | |
| 6,120,791 A | 9/2000 | Aguadisch et al. | 424/443 |
| 6,120,802 A | 9/2000 | Breitenbach et al. | |
| 6,123,861 A | 9/2000 | Santini, Jr. et al. | |
| 6,217,895 B1 | 4/2001 | Guo et al. | |
| 6,242,058 B1 | 6/2001 | Bahadur et al. | 427/515 |
| 6,267,154 B1 | 7/2001 | Felicelli et al. | |
| 6,283,951 B1 * | 9/2001 | Flaherty et al. | 604/529 |
| 6,331,313 B1 | 12/2001 | Wong et al. | |
| 6,368,658 B1 | 4/2002 | Schwarz et al. | |
| 6,375,972 B1 | 4/2002 | Guo et al. | |
| 6,491,683 B1 | 12/2002 | Dong et al. | 604/892.1 |
| 6,548,078 B2 | 4/2003 | Guo et al. | |
| 6,719,751 B2 | 4/2004 | Dong et al. | |
| 6,916,788 B2 | 7/2005 | Seo et al. | |
| 8,252,307 B2 | 8/2012 | Ashton | |
| 8,574,613 B2 | 11/2013 | Guo et al. | |
| 8,574,659 B2 | 11/2013 | Guo et al. | |
| 2001/0047012 A1 | 11/2001 | DeSantis | |
| 2002/0119197 A1 | 8/2002 | Dyar et al. | 424/473 |
| 2003/0069560 A1 * | 4/2003 | Adamis et al. | 604/521 |
| 2003/0105121 A1 | 6/2003 | Bihari et al. | |
| 2004/0009222 A1 | 1/2004 | Chou et al. | |
| 2004/0176341 A1 | 9/2004 | Chou et al. | |
| 2008/0145407 A1 | 6/2008 | Huang et al. | |
| 2010/0080830 A1 | 4/2010 | Ashton et al. | |
| 2010/0119694 A1 | 5/2010 | Guo et al. | |

FOREIGN PATENT DOCUMENTS

| | | |
|---|---|---|
| EP | 0 147 780 A2 | 7/1985 |
| EP | 0 180 708 A1 | 5/1986 |
| EP | 0 316 838 A1 | 5/1989 |
| EP | 0462959 | 6/1991 |
| EP | 0861659 A1 | 9/1998 |
| EP | 0 891 769 A1 | 1/1999 |

(56) References Cited

FOREIGN PATENT DOCUMENTS

| | | |
|---|---|---|
| HU | 210 461 | 4/1995 |
| JP | 58035110 A | 3/1983 |
| JP | H0436233 B2 | 6/1992 |
| JP | 07-048246 A | 2/1995 |
| JP | 8253426 A | 10/1996 |
| JP | 10-182499 A | 7/1998 |
| TW | 396043 | 7/2000 |
| TW | 470655 | 1/2002 |
| WO | WO-84/00296 A1 | 2/1984 |
| WO | WO-91/11176 A1 | 8/1991 |
| WO | WO-92/07556 A1 | 5/1992 |
| WO | WO-9418956 A1 | 9/1994 |
| WO | WO-95/20567 A1 | 8/1995 |
| WO | WO-9535131 A1 | 12/1995 |
| WO | WO 97/11655 | 4/1997 |
| WO | WO9715293 | 5/1997 |
| WO | WO-98/42317 A2 | 10/1998 |
| WO | WO-98/43611 A1 | 10/1998 |
| WO | WO-99/11244 A1 | 3/1999 |
| WO | WO0180825 | 11/2001 |
| WO | WO0205788 | 1/2002 |
| WO | WO-02/087586 A * 11/2002 ............... A61K 9/52 | |
| WO | WO-03051328 A1 | 6/2003 |
| WO | WO-03/094888 A1 | 11/2003 |
| WO | WO-03/098833 A2 | 11/2003 |

OTHER PUBLICATIONS

International Search Report for PCT/US2004/035430 dated Aug. 12, 2005.
Yang et al., An Intravitreal Sustained-Release Triamcinolone and 5-Fluorouracil Codrug in the Treatment of Experimental Proliferative Vitreoretinopathy, Arch Opthalmol, 116:69-77 (1998).
Baker et al., In Vitro and In Vivo Evaluation of Intravitreal Sustained Release Dexamethasone Devices; IOVS 34(4): 121-122 (1993).
Barre-Sinoussi, et al., Science, 220:868-70 (1983).
Beer et al., Intraocular concentration and pharmacokinetics of triamcinolone acetonide after a single intravitreal injection; Ophthalmology 110(4): 681-6 (2003).
Blanford et al., 5-Fluorouracil Sustained Release Device Implantation: Toxicology and Histology in Rabbits, Invest. Opthal. and vis. Sci. 31(4):591, abstr. 2893-89 (1990). (Abstract).
Challa, et al. Exudative Macular Degeneration and Intravitreal Triamcinolone: 18 Month Follow Up. Australian and New Zealand Journal of Ophthalmology, 26(4):277-281 (1998).
Cheng et al., Intravitreal Sustained-Release Dexamethasone Device in the Treatment of Experimental Uveitis; Invest. Ophthal. & Visual Science 36(2): 442-453 (1995).
Dalgleish, et al., Nature, 312:763-67 (1984).
Database WPI, Week 7943, Derwent Publications Ltd., London, GB; AN 79-78139b XP002065720 & JP 54119 020 (Nippon Kayaku KK), Sep. 14, 1979 (Absract).
Driot et al.,Ocular Pharmacokinetics of fluocinolone acetonide after Retisert intravitreal implantation in rabbits over a 1-year period; J Ocul Pharm. Ther 20(3): 269-75 (2004).
European Search Report for EP 08 16 1489 mailed Jun. 15, 2009.
Gallo, et al., Science, 224:500-3 (1984).
Goins et al., "Intravitreal Sustained Release of Gancyclovir," Invest. Opthal. and Vis. Sci. 31(4):364, abstr. 1791 (1990). (Abstract).
Hainsworth et al., Sustained Release Intravitreal Dexamethasone; J. Ocular Pham and Ther. 12: 57-63 (1996).
Jaffe et al. Safety, Efficacy, and Pharmacokinetics of an Intravitreal Fluocinolone Sustained Drug Delivery System. Abstract, Inflammation, Trauma, Toxicity Paper Presentation.
Jaffe et al. Safety, Efficacy, and Pharmacokinetics of an Intravitreal, Fluocinolone Sustained Drug Delivery System. Investigative Ophthalmology & Visual Science. 40(4):S988. (1999).
Jaffe et al., Dexamethasone Sustained Drug Delivery Implant for the Treatment of Sever Uveitis; Brief Reports 20(4): 402-403 (2000).
Klatzmann, et al., Nature, 312:767-68 (1984).
Maddon, et al., Cell, 47:333-48 (1986).
Newell et al., Clearance and Metabolism of Intravitreal Triamcinolone; IOVS 34(4): 116 (1993).
Pearson et al. Clearance and Distribution of Ciprofloxacin After Intravitreal Injection. Retina. 13(4):326-330. (1993).
Pearson et al. Evaluation of a Delivery System Providing Long-Term Release of Cyclosporine. Arch Ophthamology. 114:311-17 (1996).
Pearson et al., "Polyvinyl Alcohol Membrane Permeability Characteristics of Gancyclovir," Invest. Opthal. and Vis. Sci. 30(4):511, abstr. 42 (1989). (Abstract).
Pearson et al., Proceed. Intern. Symp. Control Rel. Bioch. Mater. 17 (1990) Controlled Release Society, Jul. 22-25, pp. 470, 171.
Perasalo. The Prevalence of Macular Degeneration in a Cohort of Institutionalized Geriatric Glaucoma Patients. Acta Ophthamology. 72(2):175-77 (1994).
Rafii et al., Pharmacokinetics of Sustained-Release Implantable Devices of Acetazolamide; IOVA 34(4): 121-122 (1993).
Smith et al., "A Membrane Based Sustained Release Ocular Delivery System for 5-Fluorouracil," Invest. Opthal. and Vis. Sci. 30(4):271, abstr. 37 (1989) (Abstract).
Smith et al., "Intraocular Sustained Release of Antiviral Agents in AIDS," Proceed. Intern. Symp. Contol. Rel. Bioact. Mater. 17:470-471 (1990).
Smith et al., "Polyvinyl Alcohol Membrane Permeability Characteristics of 5-Fluorouracil," Journal of Ocular Pharmacology 4(2):147-152 (1988).
Solomon et al., "Sustained Release Drug Delivery Systems in Extracapsular Cataract Surgery," Invest. Opthal. and Vis. Sci. 31(4):351 Abstr. 1724-19 (1990) (Abstract).
International Search Report for PCT/US00/07513 mailed Aug. 30, 2000.
International Search Report for PCT/US01/12700 mailed Apr. 18, 2002.
ROC (Taiwan) Search Report dated Jan. 18, 2011 for Patent Application No. 093133899.
Goodman & Gilman's The Pharmacological Basis of Therapeutics, 1996, "Adrenocorticotropic Hormone; Adrenocortical Steroids and their synthetic analogs; inhibitors of the synthesis and actions of synthesis and actions of adrenocortical hormones", Schimmer, B.P. and Parker, K.L., chapter 59, pp. 1459, 1473, 1474, 1480, and "Ocular Pharmacology", Moroi, S.E. and Lichter, P.R. chapter 65, pp. 1619, 1636 and 1637.
Haynes et al., "Effect of Inhibitors of Arachidonic Acid Metabolism on Corneal Neovascularization in the Rat," Investigative Ophthalmology & Visual Science, 30(7):1588-1593 (1989).
Tano et al., "Inhibition of Intraocular Proliferations With Intravitreal Corticosteriods," American Journal of Ophthalmology, 89(1):131-135 (1980).

* cited by examiner

INJECTABLE SUSTAINED RELEASE DELIVERY DEVICES

RELATED APPLICATIONS

This application is a continuation-in-part of U.S. patent application Ser. No. 10/428,214, filed May 2, 2003 now abandoned, which claims the benefit of U.S. Prov. App. No. 60/452,348, filed on Mar. 6, 2003, U.S. Prov. App. No. 60/437,576, filed on Dec. 31, 2002, and U.S. Prov. App. No. 60/377,974, filed on May 7, 2002. This application is also related to Patent Cooperation Treaty App. No. US03/13733, filed on May 1, 2003. This application also claims the benefit of U.S. Application No. 60/425,943, filed on Nov. 13, 2002. The teachings of each of the above applications is incorporated herein by reference.

BACKGROUND

1. Field of the Invention

The present invention relates to injectable sustained release drug delivery devices, and processes useful for making such devices.

2. Brief Description of the Related Art

U.S. Pat. No. 6,375,972, by Hong Guo et al., incorporated by reference herein in its entirety, describes certain drug delivery devices using various combinations of drug cores and polymer coatings to control a delivery rate of drugs implanted into living tissue. While having significant advantages, the reduction in the size of such devices as a part of a normal product development cycle can make manufacture of the devices more difficult. As described in the '972 patent, the drug reservoir can be formed within the tube which supports it by a number of different methods, including injecting the drug matrix into the preformed tube. With smaller tubes and more viscous drug matrix materials, this technique becomes increasingly difficult.

One approach to this difficulty is disclosed in an article by Kajihara et al. appearing in the Journal of Controlled Release, 73, pp. 279-291 (2001), which describes the preparation of sustained-release formulations for protein drugs using silicones as carriers. The disclosure of this article is incorporated herein in its entirety.

Another approach to reducing the size of sustained-release drug delivery systems is disclosed in U.S. pat. app. Ser. No. 10/428,214, filed May 2, 2003. While that disclosure is not limited to devices of any particular size, the co-extrusion techniques disclosed therein are amenable to the manufacture of small devices.

Despite the inherent difficulties in manufacturing small, sustained-release drug delivery devices, such devices have started to approach sizes where injection of the device becomes a possibility. However, there remains a need for improved injectable sustained-release drug delivery systems and techniques for making the same.

SUMMARY OF THE INVENTION

An injectable drug delivery device includes a core containing one or more drugs and one or more polymers. The core may be surrounded by one or more polymer outer layers (referred to herein as "coatings," "skins," or "outer layers"). In certain embodiments, the device is formed by extruding or otherwise preforming a polymeric skin for a drug core. The drug core may be co-extruded with the skin, or inserted into the skin after the skin has been extruded, and possibly cured. In other embodiments, the drug core may be coated with one or more polymer coatings. These techniques may be usefully applied to fabricate devices having a wide array of drug formulations and skins that can be selected to control the release rate profile and various other properties of the drugs in the drug core in a form suitable for injection using standard or non-standard gauge needles. The device may be formed by combining at least one polymer, at least one drug, and at least one liquid solvent to form a liquid suspension or solution wherein, upon injection, such suspension or solution under goes a phase change and forms a gel. The configuration may provide for controlled release of the drug(s) for an extended period.

In embodiments using a skin, the skin may be permeable, semi-permeable, or impermeable to the drug, or to the fluid environment to which the device may be exposed. The drug core may include a polymer matrix which does not significantly affect the release rate of the drug. Alternatively, such a polymer matrix may affect the release rate of the drug. The skin, the polymer matrix of the drug core, or both may be bioerodible. The device may be fabricated as an extended mass that is segmented into drug delivery devices, which may be left uncoated so that the drug core is exposed on all sides or (where a skin is used) at the ends of each segment, or coated with a layer such as a layer that is permeable to the drug, semi-permeable to the drug, impermeable, or bioerodible.

BRIEF DESCRIPTION OF THE DRAWINGS

The invention of the present application will now be described in more detail with reference to the accompanying drawings, wherein like reference numerals designate identical or corresponding elements.

DETAILED DESCRIPTION

To provide an overall understanding of the invention, certain illustrative embodiments will now be described, including systems and methods for injectable sustained release drug delivery devices having cylindrical cross-sections fabricated using extrusion. However, it will be understood that the systems and methods described herein may be usefully applied to a number of different devices, such as devices with various cross-sectional geometries or devices with two- or more concentrically aligned or non-concentrically aligned cores of different active agents. It will further be appreciated that various combinations of any of the drugs and outer layers described herein, or other drugs or outer layers not specifically mentioned herein, are within the scope of this disclosure and may be usefully employed in an injectable drug delivery device of the present invention. In still other embodiments, the invention may readily be adapted to the injectable delivery of drugs through the use of in situ gelling formulations and other delivery devices such as liquid suspensions. All such embodiments are intended to fall within the scope of the invention described herein.

Figure 1:
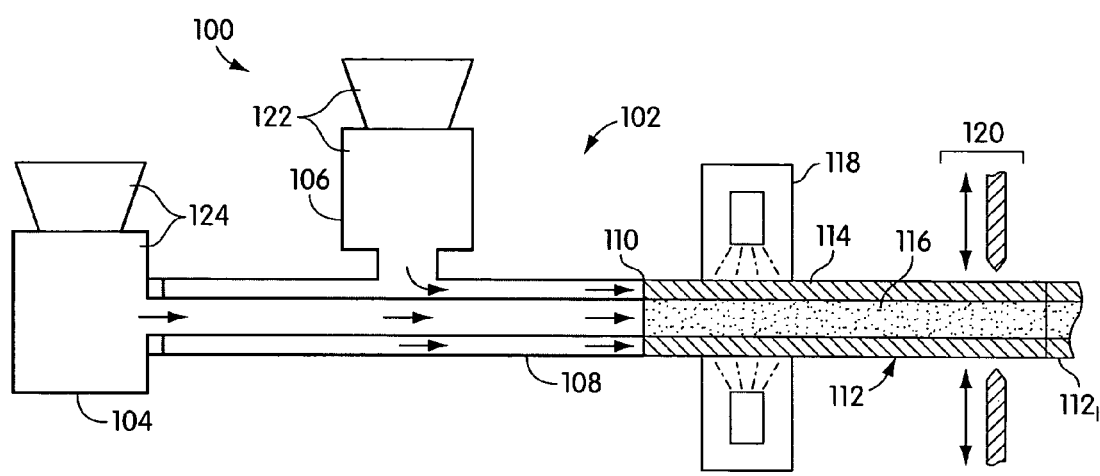
FIG. 1 shows an apparatus for co-extruding drug delivery devices.
Figure 2:
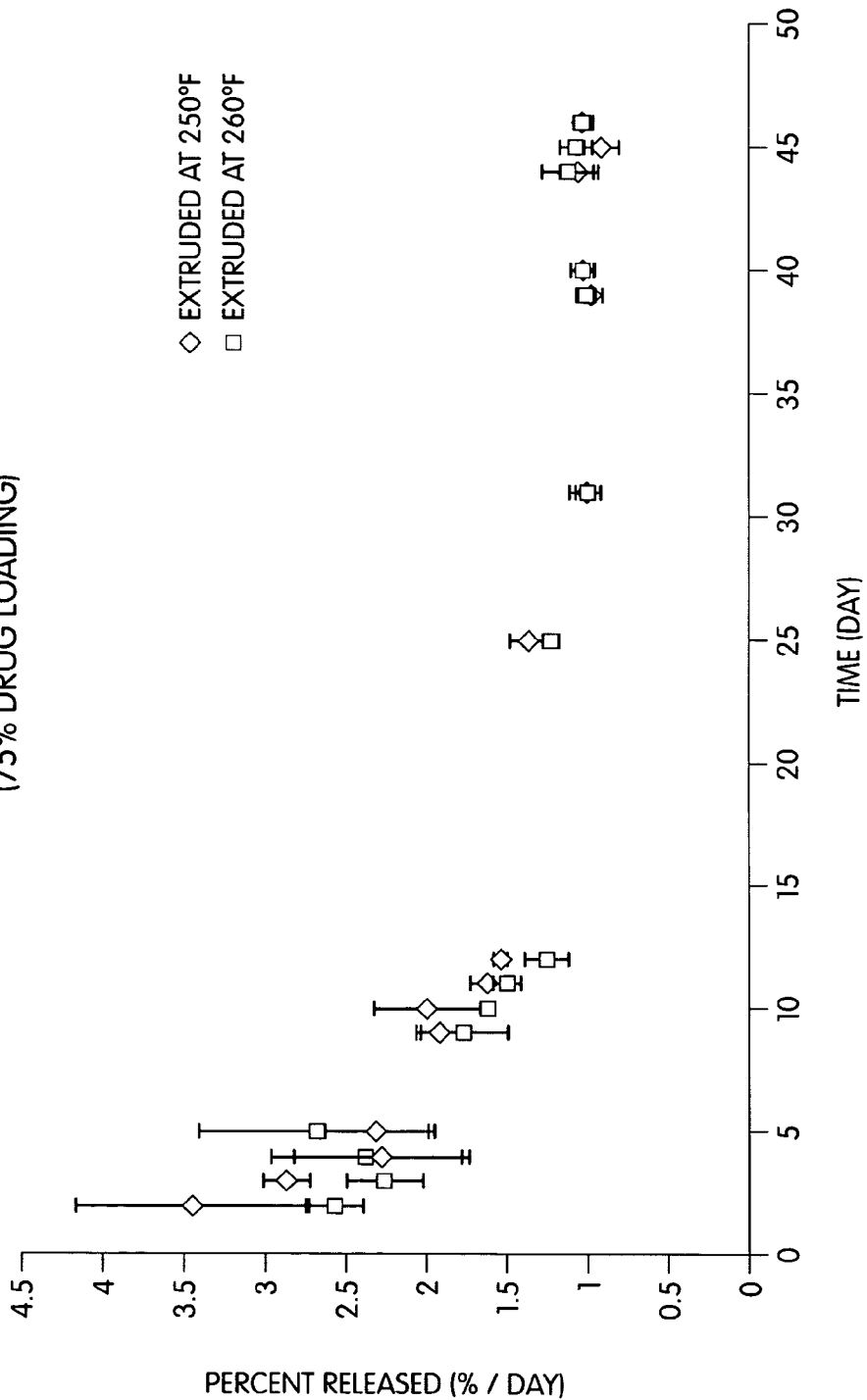
FIGS. 2-5 show release rates of various extruded formulations.
Figure 3:
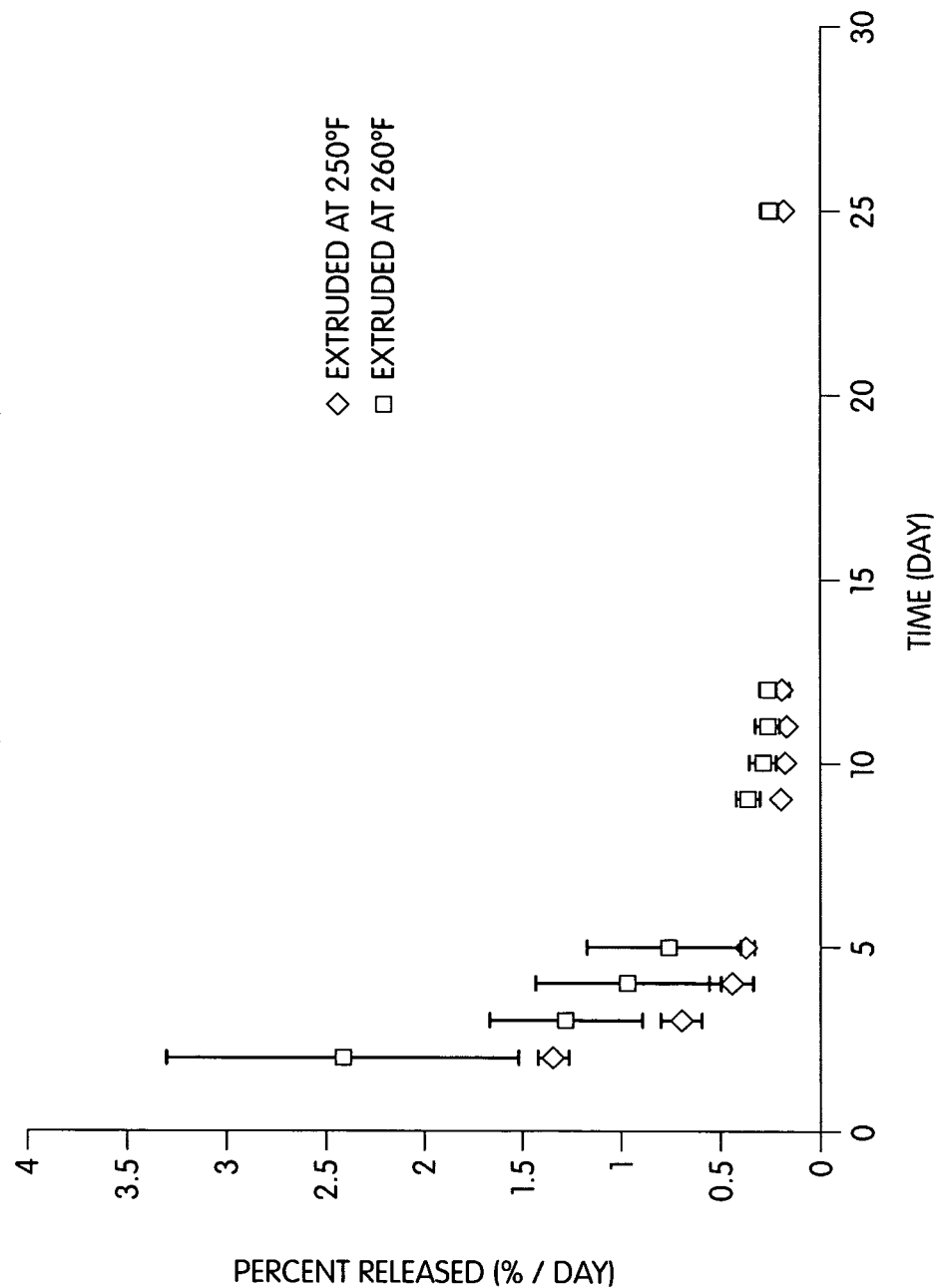
Figure 4:
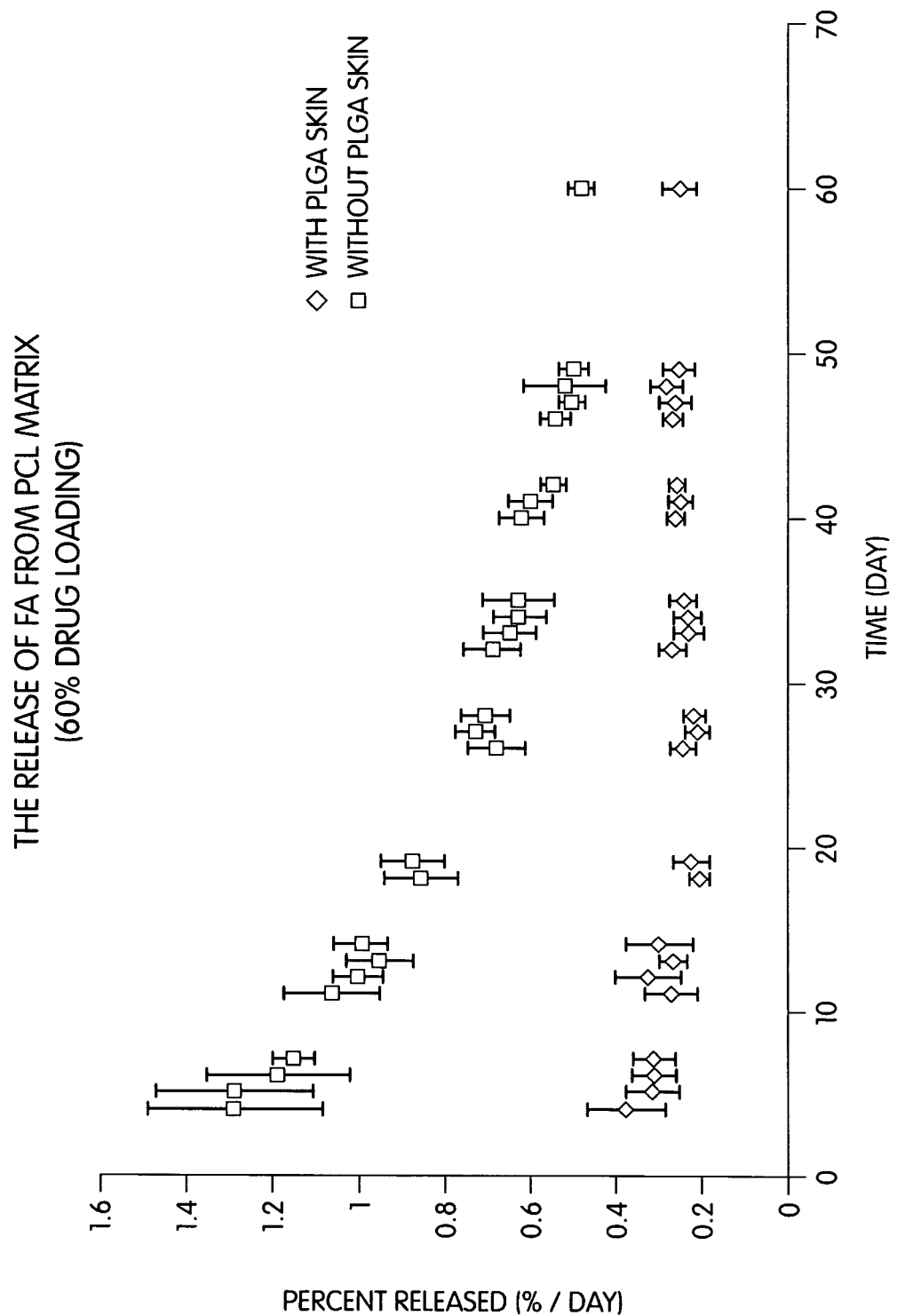
Figure 5:
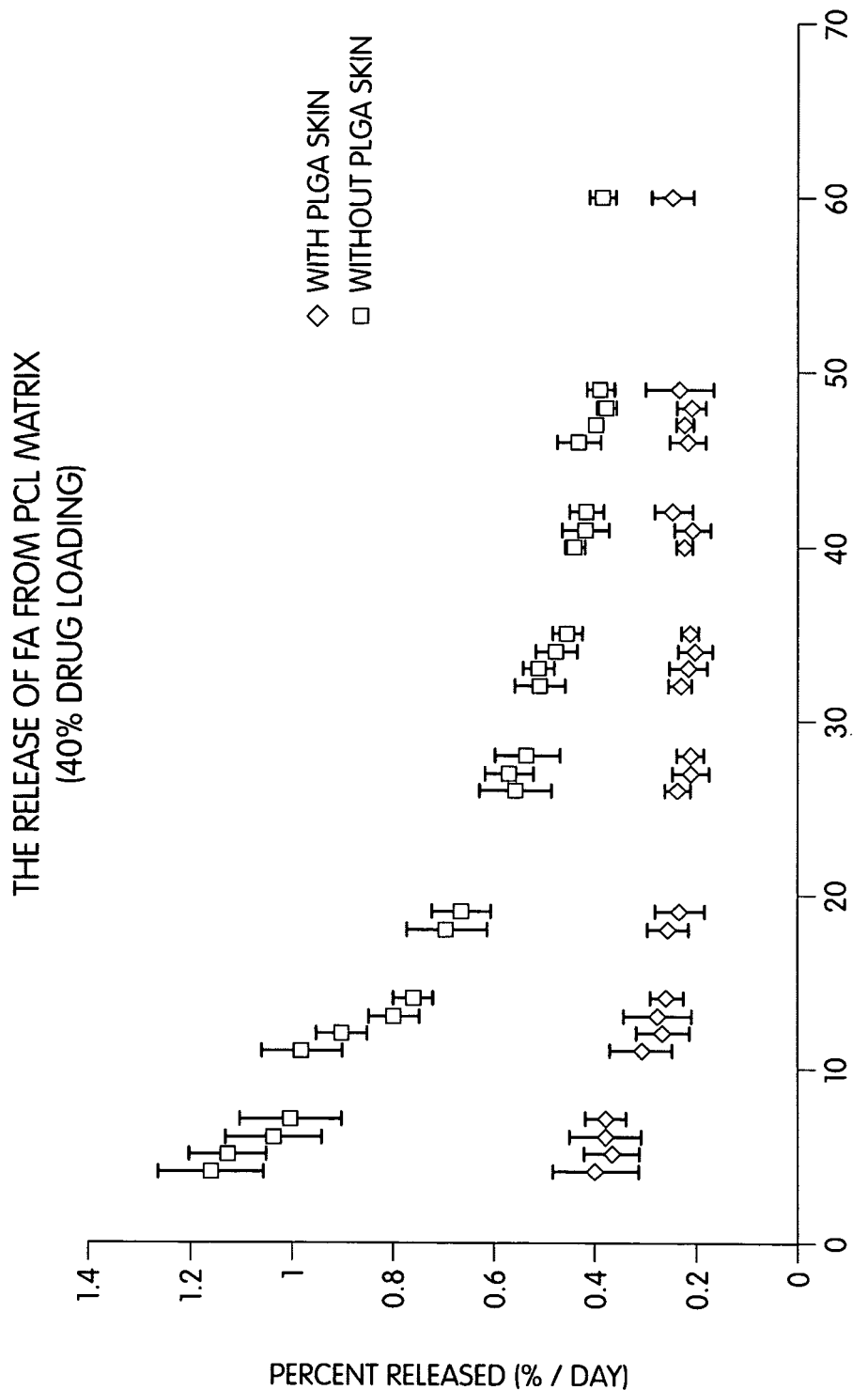

FIG. 1 shows an apparatus for co-extruding drug delivery devices. As illustrated in FIG. 1, a system 100 may include a co-extrusion device 102 including at least a first extruder 104 and a second extruder 106, both of which are connected to a die head 108 in a manner well known to those of skill in the extrusion arts. The die head 108 has an exit port 110 out of which the co-extruded materials from the extruders 104, 106 are forced. The die head 108 and/or exit port 110 may establish a cross-sectional shape of extruded matter. Suitable commercially available extruders for use as the extruders 104, 106 include the Randcastle model RCP-0250 Microtruder (Randcastle Extrusion Systems, Cedar Grove, N.J.), and its associated heaters, controllers, and associated hardware. Exemplary extruders are also disclosed, for example, in U.S. Pat. Nos. 5,569,429, 5,518,672, and 5,486,328.

The extruders 104, 106 may extrude a material through the die head 108 in a known manner, forming a composite co-extruded product 112 which exits the die head 108 at the exit port 110. Each extruder 104, 106 may extrude more than one material through the die head 108 to form a composite co-extruded product 112. The system 100 may also have more than two extruders for extruding, e.g., adjacent or concentric drug matrices or additional outer layers. The product 112 may include a skin 114 and a core 116. As described in greater detail herein, the skin 114 may be (or be the precursor to) the drug impermeable tube 112, 212, and/or 312 in the aforementioned '972 patent's devices, and the core 116 may be (or may be the precursor to) the reservoir 114, 214, and/or 314 in the '972 patent's devices.

In general, the co-extruded product 112 may have an outside diameter suitable for use with a needle ranging in size from about a 30 gauge needle to about a 12 gauge needle, or with a needle ranging in inside diameter from about 0.0055 inches to about 0.0850 inches. It will be appreciated that the co-extruded product 112 may be coated with one or more additional layers, and that the initial size may be such that the coated device has an outside diameter corresponding to a specific needle size. It will also be appreciated that the range of needle sizes is exemplary only, and that the systems described herein may be used to manufacture injectable devices for use with larger or smaller needles than those specifically recited above. It should further be appreciated that the term "injectable devices" as used herein, does not refer strictly to devices that are injectable using only hypodermic needle sizes described above. Rather, the term is intended to be construed broadly, and may include devices that are administered through an arthroscope, catheter, or other medical device. Similarly, the terms "inject" and "injected" are meant to include administration by means more broad than via hypodermic needle, such as by arthroscope, catheter, or other medical device. In certain embodiments, the device may be injected in the vicinity of a patient's eye as either an intraocular or periocular injection.

In an extrusion process, extrusion parameters may be controlled, such as fluid pressure, flow rate, and temperature of the material being extruded. Suitable extruders may be selected for the ability to deliver the co-extruded materials at pressures and flow rates sufficient to form the product 112 at sizes of the die head 108 and exit port 110 which will produce a product which, when segmented, can be injected into a patient. The term "patient," as used herein, refers to either a human or a non-human animal. As described in greater detail below, the choice of materials that are to be extruded through the extruders 104, 106 may also affect the extrusion process and implicate additional parameters of the extrusion process, as well as of the overall system 100.

The system 100 may include additional processing devices that provide further processing of the materials extruded by the extruders 104, 106, and/or the extruded product 112. By way of example and not of limitation, the system 100 may further include a curing station 118 which at least partially cures the product 112 as it passes through the station. The curing station 118 may cure either the skin 114, the core 116, or both, and may operate continuously on the extruded product 112 as it passes through the curing station 118, or in intervals coordinated with the passage of extruded material. The curing station 118 may apply heat, ultraviolet radiation, or some other energy suitable for curing the polymers in the product 112. It will be appreciated that corresponding curable polymers, such as heat curable polymers or radiation curable polymers may be employed in the skin 114 and/or the core 116. Generally, the degree of curing may be controlled by controlling an amount of energy applied by the curing station 118.

A segmenting station 120 may be provided which segments or otherwise cuts the product 112 into a series of shorter products $112_f$. The segmenting station 120 may use any suitable technique for cutting the extruded product 112, which may vary according to whether the product 112 is cured, uncured, or partially cured. For example, the segmenting station 120 may employ pincers, shears, slicing blades, or any other technique. The technique applied by the segmenting station 120 may vary according to a configuration desired for each cut portion of the product 112. For example, where open ends are desired for addition of a diffusion membrane or other functional coating, a shearing action may be appropriate. However, where it is desired to seal each end as the cut is made, a pincer may be used. Multiple cutting instruments may be provided where different cuts are desired for each end, or for different groups of shorter products $112_f$.

Suitable materials 122, 124 for use with the co-extrusion device 102 to form the skin 114 and the core 116, respectively, are numerous. In this regard, the '972 patent describes a number of suitable materials for forming implantable drug delivery devices, which materials may be more specifically used for injectable drug delivery devices. Preferably, the materials used as materials 122, 124 are selected for their ability to be extruded through the system 100 without negatively affecting the properties for which they are specified. For example, for those materials which are to be impermeable to the drugs within the core 116, a material is selected which, upon being processed through an extrusion device, is or remains impermeable. Similarly, biocompatible materials may be selected for the materials which will, when the drug delivery device is fully constructed, come in contact with the patient's biological tissues. Suitable polymers for use as materials 122, 124 include, but are not limited to, poly(caprolactone) (PCL), ethylene vinyl acetate polymer (EVA), poly(ethylene glycol) (PEG), polyvinyl alcohol (PVA), poly(lactic acid) (PLA), poly(glycolic acid) (PGA), poly(lactic-co-glycolic acid) (PLGA), polyalkyl cyanoacrylate, polyurethane, nylons, or copolymers thereof. In polymers including lactic acid monomers, the lactic acid may be D-, L-, or any mixture of D- and L-isomers.

In addition to polymers, non-aqueous solvents such as PEG may be usefully employed as materials 122, 124 in preparing the core 116. For example, non-aqueous solvents that dissolve polymer used in the core 116, that cause a phase change of the core 116, or that ease extrusion (e.g., by providing a greater working temperature range) or other processing of the product 112 may be usefully employed.

Certain extrusion parameters may be dictated or suggested by a selection of the material(s) 124 which are to be fed into the extruder 104 to form the inner drug core 116. As one of skill in the art will readily appreciate, extrusion devices typically include one or more heaters and one or more screw drives, plungers, or other pressure-generating devices. It may be a goal of the extruder to raise the temperature, fluid pressure, or both, of the material being extruded. This can present difficulties when a pharmaceutically active drug is included in the materials being processed and extruded by the extruder 104. The active drug may be heated and/or exposed to elevated pressures that negatively affect its efficacy. This difficulty can be compounded when the drug itself is to be held in a polymer matrix, and therefore a polymer material is also mixed and heated and/or pressurized with the drug in the extruder 104. The materials 124 may be selected so that the activity of the drug in core 116 of the product 112 is sufficient for producing the desired effect when injected. Furthermore, when the drug is admixed with a polymer for forming a matrix in the extruded core 116, the polymer material which forms the matrix may be advantageously selected so that the drug is not destabilized by the matrix. The matrix material may be selected so that diffusion through the matrix has little or no effect on the release rate of the drug from the matrix. Also, the particle size of the drug(s) used in the matrix may be selected to have a controlling effect on dissolution of the drug(s).

The materials 122, 124, from which the product 112 is co-extruded, may be selected to be stable during the release period for the drug delivery device. The materials may optionally be selected so that, after the drug delivery device has released the drug for a predetermined amount of time, the drug delivery device erodes in situ, i.e., is bioerodible. The materials may also be selected so that, for the desired life of the delivery device, the materials are stable and do not significantly erode, and the pore size of the materials does not change. Optionally, either or both of the materials 122, 124 may be chosen to be bioerodible at rates that control, or contribute to control of, the release rate of any active agents. It will be appreciated that other materials, such as additional coatings on some or all of the device may be similarly selected for their bioerodible properties.

Thus in one respect, there is described herein a process for selecting materials to be used in a co-extrusion process for fabricating injectable drug delivery devices. In general, the material selection process for materials 122, 124 may proceed as follows: (1) one or more drugs are selected; (2) an extrudable material or class of materials is selected; (3) the material or class of materials is evaluated to ascertain whether and how it affects the release rate of the chosen drug(s) from the material or class of materials; (4) the stability and physico-chemical properties of the material or class of materials are evaluated; (5) the stability of the drug within a matrix of the material or class of materials is evaluated; and (6) the material or class of materials is evaluated to ascertain whether, when formed into a matrix with the chosen drug(s), the material or class of materials prevents biological molecules (e.g., proteinaceous materials) from migrating into the matrix and interacting with the drug(s). Thus, there are at least two functions of the inner material: to permit co-extrusion or extrusion of the core; and to inhibit, or prevent, erosion or degradation of the drug in the core. An advantage of the system is that the differences between the release rates of drug from delivery devices into different environments, such as different tissue types or different disease conditions, can be controlled.

The materials 122, 124 may include one or multiple pharmaceutically active drugs, matrix-forming polymers, any biomaterials such as lipids (including long chain fatty acids) and waxes, anti-oxidants, and in some cases, release modifiers (e.g., water or surfactants). These materials may be biocompatible and remain stable during the extrusion processes. The blend of active drugs and polymers should be extrudable under the processing conditions. The matrix-forming polymers or any biomaterials used may be able to carry a sufficient amount of active drug or drugs to produce therapeutically effective actions over the desired period of time. It is also preferred that the materials used as drug carriers have no deleterious effect, or no significant deleterious effect, on the activity of the pharmaceutical drugs.

Polymers employed within the skin 114 and the core 116, or coatings added to the skin 114 and/or core 116, may be selected with respect to permeability to one or more drugs within the core 116. Permeability is necessarily a relative term. As used herein, the term "permeable" is intended to mean permeable or substantially permeable to a substance, which is typically the drug that the device delivers unless otherwise indicated (for example, where a membrane is permeable to a biological fluid from the environment into which a device is delivered). As used herein, the term "impermeable" is intended to mean impermeable or substantially impermeable to substance, which is typically the drug that the device delivers unless otherwise indicated (for example, where a membrane is impermeable to a biological fluid from the environment into which a device is delivered). The term "semi-permeable" is intended to mean selectively permeable to some substances but not others. It will be appreciated that in certain cases, a membrane may be permeable to a drug, and also substantially control a rate at which the drug diffuses or otherwise passes through the membrane. Consequently, a permeable membrane may also be a release-rate-limiting or release-rate-controlling membrane, and in certain circumstances, permeability of such a membrane may be one of the most significant characteristics controlling release rate for a device. Thus, if part of a device is coated by a permeable coating and the rest of the device is covered by an impermeable coating, it is contemplated that, even though some drug may pass through the impermeable coating, the drug will predominately be released through the part of the device coated only with the permeable coating.

The polymers or other biomaterials used as active drug carriers may be selected so that the release rate of drugs from the carriers are determined by the physico-chemical properties of the drugs themselves, but not by the properties of the drug carriers. The active drug carrier may also be selected to be a release modifier, or a release modifier may be added to tailor the release rate. For example, organic acid, such as citric acid and tartaric acid, may be used to facilitate the diffusion of weak basic drugs through the release medium, while the addition of amines such as triethanolamine may facilitate the diffusion of weak acidic drugs. Polymers with an acidic or basic pH value may also be used to facilitate or attenuate the release rate of active drugs. For example, PLGA may provide an acidic micro-environment in the matrix, since it has an acidic pH value after hydrolysis. For a hydrophobic drug, a hydrophilic agent may be included to increase its release rate.

Surfactants may also be employed in the material that forms the core 116 in order to alter the properties thereof The charge, lipophilicity or hydrophilicity of any polymeric matrix in the core 116 may be modified by incorporating in some fashion an appropriate compound in the matrix. For example, surfactants may be used to enhance wettability of poorly soluble or hydrophobic compositions. Examples of suitable surfactants include dextran, polysorbates and sodium lauryl sulfate. More generally, the properties and uses of surfactants are well known, and may be advantageously incorporated into the core 116 in certain drug delivery applications of the present invention.

Processing parameters for co-extrusion will now be discussed in greater detail.

Temperature: The processing temperature (extrusion temperature) should be below the decomposition temperatures of active drug, polymers, and release modifiers (if any). The temperature may be maintained such that the matrix-forming polymers are capable of accommodating a sufficient amount of active drug to achieve the desired drug loading. For example, PLGA can carry up to 55% of fluocinolone acetonide (FA) when the drug-polymer blends are extruded at 100° C., but 65% at 120° C. The drug-polymer blends should display good flow properties at the processing temperature to ensure the uniformity of the final products and to achieve the desired draw ratio so the size of the final products can be well controlled.

Screw Speed: The screw speeds for the two extruders in the co-extrusion system may be set at speeds at which a predetermined amount of polymeric skin 114 is co-extruded with the corresponding amount of drug-core 116 materials to achieve the desired thickness of polymeric skin 114. For example: 10% weight of PCL skin 114 and 90% weight of FA/PCL drug core 116 can be produced by operating extruder 106 at a speed nine times slower than that of extruder 104 provided that the extruders 104 and 106 have the same screw size. Different screw sizes may also be used, with suitable adjustments to speed thereof.

A drug or other compound can be combined with a polymer by dissolving the polymer in a solvent, combining this solution with the drug or other compound, and processing this combination as necessary to provide an extrudable paste. Melt-granulation techniques, including solventless melt-granulation, with which those of skill in the art are well acquainted, may also be employed to incorporate drug and polymer into an extrudable paste.

FIGS. 2-5 show release rates of various extruded formulations. The release rate of FA from a FA/PCL (e.g., 75/25) or FA/PLGA (e.g., 60/40) core matrix with no co-extruded polymeric skin both showed a bi-phase release pattern: a burst release phase, and a slow release phase (see FIGS. 2 and 3). The burst release phase was less pronounced when FA levels (loading) in the PCL matrix were reduced from 75% to 60% or 40% (compare FIG. 2 with FIGS. 3-5). A review of the data presented in FIGS. 3 and 4 reveals that the time to reach near zero-order release for the co-extrusion preparation (drug in a polymer matrix with a PLGA skin) was much shorter than the preparation without a PLGA skin coat. A co-extruded FA/polymer core matrix with PLGA as a skin coat can significantly minimize the burst effect, as demonstrated by FIGS. 4 and 5.

The segmented drug delivery devices may be left open on one end, leaving the drug core exposed. The material 124 which is co-extruded to form the drug core 116 of the product 112, as well as the co-extrusion heats and pressures and the curing station 118, may be selected so that the matrix material of the drug core inhibits or prevents the passage of enzymes, proteins, and other materials into the drug core which would lyse the drug before it has an opportunity to be released from the device. As the core empties, the matrix may weaken and break down. Then the skin 114 will be exposed to degradation from both the outside and inside from water and enzymatic action. Drugs having higher solubility may be linked to form low solubility conjugates using the techniques described in U.S. Pat. No. 6,051,576, as further discussed below; alternatively, drugs may be linked together to form molecules large enough to be retained in the matrix.

The material 122 from which the skin 114 is formed may be selected to be curable by a non-heat source. As described above, some drugs may be negatively affected by high temperatures. Thus, one aspect of the system relates to the selection and extrusion of a material which can be cured by methods other than heating, including, but not limited to, catalyzation, radiation and evaporation. By way of example and not of limitation, materials capable of being cured by electromagnetic (EM) radiation, e.g., in the visible or near-visible ranges, e.g., of ultraviolet or blue wavelengths, may be used, or included in, material 122. In this example, the curing station 118 may include one or more corresponding sources of the EM radiation which cure the material, such as an intense light source, a tuned laser, or the like, as the product 112 advances through the curing station 118. By way of example and not of limitation, curable acrylic based adhesives may be used as material 122.

Other parameters may affect the release rate of drug from the drug core 116 of an injectable drug delivery device, such as the pH of the core matrix. The materials 124 of the drug core may include a pH buffer or the like to adjust the pH in the matrix to further tailor the drug release rate in the finished product 112. For example, organic acid, such as citric, tartaric, and succinic acid may be used to create an acidic micro-environment pH in the matrix. The constant low pH value may facilitate the diffusion of weak basic drug through the pores created upon dissolution of the drug. In the case of a weak acidic drug, an amine, such as triethanolamine, may be used to facilitate drug release rates. A polymer may also be used as a pH-dependent release modifier. For example, PLGA may provide an acidic micro-environment in the matrix as it has an acid pH value after hydrolysis.

More than one drug may be included in the material 124, and therefore in the core 116 of the product 112. The drugs may have the same or different release rates. As an example, 5-fluorouracil (5-FU) is highly water-soluble and it is difficult to sustain a controlled release of the drug. On the other hand, steroids such as triamcinolone acetonide (TA) are much more lipophilic and may provide a slower release profile. When a mixture of 5-FU and TA forms a pellet (either by compression or by co-extrusion), the pellet provides a controlled release of 5-FU over a 5-day period to give an immediate, short-term pharmaceutical effect while simultaneously providing a controlled release of TA over a much longer period. Accordingly, a mixture of 5-FU and TA, and/or codrugs or prodrugs thereof, alone or with other drugs and/or polymeric ingredients, may be extruded to form the core 116.

In addition to the embodiments illustrated above, those skilled in the art will understand that any of a number of devices and formulations may be adopted for use with the systems described herein. The core may comprise a biocompatible fluid or oil combined with a biocompatible solid (e.g., a bioerodible polymer) and an active agent. In certain embodiments, the inner core may be delivered as a gel while, in certain other embodiments, the inner core may be delivered as a particulate or a liquid that converts to a gel upon contact with water or physiological fluid. Examples of this type of system are described for example, in U.S. Provisional Application No. 60/501,947, filed Sep. 11, 2003. The '947 application also provides for the delivery of injectable liquids that, upon injection, undergo a phase transition and are transformed in situ into gel delivery vehicles. Such liquids may be employed with the injectable devices described herein.

Injectable in situ gelling compositions may be used with the systems described herein, comprising a drug substance, a biocompatible solvent (e.g., a polyethylene glycol (PEG)), and a biocompatible and bioerodible polymer. Certain embodiments of this formulation may be particularly suitable, such as those that provide for the injection of solid drug particles that are dissolved, dispersed, or suspended in the PEG, and embodiments that allow for the injection of a polymeric drug-containing gel into a patient. Examples of injectable in situ gelling compositions may be found in U.S. Prov. App. No. 60/482,677, filed Jun. 26, 2003.

The term "drug" as it is used herein is intended to encompass all agents which provide a local or systemic physiological or pharmacological effect when administered to mammals, including without limitation any specific drugs noted in the following description and analogs, derivatives, pharmaceutically acceptable salts, esters, prodrugs, codrugs, and protected forms thereof.

Many different drugs may be incorporated into the devices described herein. For example, suitable drugs include steroids, alpha receptor agonists, beta receptor antagonists, carbonic anhydrase inhibitors, adrenergic agents, physiologically active peptides and/or proteins, antineoplastic agents, antibiotics, analgesics, anti-inflammatory agents, muscle relaxants, anti-epileptics, anti-ulcerative agents, anti-allergic agents, cardiotonics, anti-arrhythmic agents, vasodilators, antihypertensive agents, anti-diabetic agents, anti-hyperlipidemics, anticoagulants, hemolytic agents, antituberculous agents, hormones, narcotic antagonists, osteoclastic suppressants, osteogenic promoters, angiogenesis suppressors, antibacterials, non-steroidal anti-inflammatory drugs (NSAIDs), glucocorticoids or other anti-inflammatory corticosteroids, s alkaloid analgesics, such as opioid analgesics, antivirals, such as nucleoside antivirals or a non-nucleoside antivirals, anti-benign prostatic hypertrophy (BPH) agents, anti-fungal compounds, antiproliferative compounds, anti-glaucoma compounds, immunomodulatory compounds, cell transport/mobility impeding agents, cytokines pegylated agents, alpha-blockers, anti-androgens, anti-cholinergic agents, purinergic agents, dopaminergic agents, local anesthetics, vanilloids, nitrous oxide inhibitors, anti-apoptotic agents, macrophage activation inhibitors, antimetabolites, neuroprotectants, calcium channel blockers, gamma-aminobutyric acid (GABA) antagonists, alpha agonists, anti-psychotic agents, tyrosine kinase inhibitors, nucleoside compounds, and nucleotide compounds, and analogs, derivatives, pharmaceutically acceptable salts, esters, prodrugs, codrugs, and protected forms thereof.

Suitable NSAIDs include diclofenac, etoldolac, fenoprofen, floctafenine, flurbiprofen, ibuprofen, indoprofen, ketoprofen, ketorolac, lomoxicam, morazone, naproxen, perisoxal, pirprofen, pranoprofen, suprofen, suxibuzone, tropesin, ximoprofen, zaltoprofen, zileuton, and zomepirac, and analogs, derivatives, pharmaceutically acceptable salts, esters, prodrugs, codrugs, and protected forms thereof.

Suitable carbonic anhydrase inhibitors include brinzolarnide, acetazolamide, methazolamide, dichlorphenamide, ethoxzolamide, and dorzolamide, and analogs, derivatives, pharmaceutically acceptable salts, esters, prodrugs, codrugs, and protected forms thereof.

Suitable adrenergic agents include brimonidine, apraclonidine, bunazosin, levobetaxolol, levobunalol, carteolol, isoprenaline, fenoterol, metipranolol, and clenbuterol, and analogs, derivatives, pharmaceutically acceptable salts, esters, prodrugs, codrugs, and protected forms thereof.

Suitable alpha receptor agonists include brimonidine and analogs, derivatives, pharmaceutically acceptable salts, esters, prodrugs, codrugs, and protected forms thereof.

Suitable beta receptor antagonists include betaxolol and timolol, and analogs, derivatives, pharmaceutically acceptable salts, esters, prodrugs, codrugs, and protected forms thereof.

Suitable antiviral agents include neviripine and analogs, derivatives, pharmaceutically acceptable salts, esters, prodrugs, codrugs, and protected forms thereof.

Suitable alkaloid analgesics include desmorphine, dezocine, dihydromorphine, eptazocine, ethylmorphine, glafenine, hydromorphone, isoladol, ketobenidone, p-lactophetide, levorphanol, moptazinol, metazocin, metopon, morphine, nalbuphine, nalmefene, nalorphine, naloxone, norlevorphanol, normorphine, oxmorphone, pentazocine, phenperidine, phenylramidol, tramadol, and viminol, and analogs, derivatives, pharmaceutically acceptable salts, esters, prodrugs, codrugs, and protected forms thereof.

Suitable glucocorticoids include 21-acetoxypregnenolone, alclometasone, algestone, anacortave acetate, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, diflorasone, diflucortolone, difuprednate, enoxolone, fluazacort, flucloronide, flumethasone, flunisolide, fluocinolone acetonide, fluocinonide, flucloronide, flumethasone, flunisolide, fluocortin butyl, fluocortolone, fluorometholone, fluperolone acetate, fluprednisolone, flurandrenolide, fluticasone propionate, hydrocortamate, hydrocortisone, meprednisone, methylprednisolone, paramethasone, prednisolone, prednisolone 21-diethylaminoacetate, fluprednidene acetate, formocortal, loteprednol etabonate, medrysone, mometasone furoate, prednicarbate, prednisolone, prednisolone 25-diethylaminoacetate, prednisolone sodium phosphate, prednisone, prednival, prednylidene, triamcinolone, triamcinolone acetonide, triamcinolone benetonide, and triamcinolone hexacetonide, and analogs, derivatives, pharmaceutically acceptable salts, esters, prodrugs, codrugs, and protected forms thereof.

Other suitable steroids include halcinonide, halbetasol propionate, halometasone, halopredone acetate, isoflupredone, loteprednol etabonate, mazipredone, rimexolone, and tixocortol, and analogs, derivatives, pharmaceutically acceptable salts, esters, prodrugs, codrugs, and protected forms thereof.

Suitable BPH drugs include finasteride and osaterone, and analogs, derivatives, pharmaceutically acceptable salts, esters, prodrugs, codrugs, and protected forms thereof.

Suitable antineoplastic compounds include alitretinoin (9-cis-retinoic acid); bleomycins, including bleomycin A; capecitabine (5'-deoxy-5-fluoro-cytidine); carubicin; chlorozotocin, chromomycins, including chromomycin $A_3$, cladribine; colchicine, cytarabine; daunorubicin; demecolcine, denopterin, docetaxel, doxyifluridine, doxorubicin; dromostanolone, edatrexate, enocitabine, epirubicin, epitiostanol, estramustine; etoposide; floxuridine, fludarabine, 5-fluorouracil, formestane, gemcitabine; irinotecan; lentinan, lonidamine, melengestrol, melphalan; menogaril, methotrexate; mitolactol; nogalamycin; nordihydroguaiaretic acid, olivomycins such as olivomycin A, paclitaxel; pentostatin; pirarubicin, plicamycin, porfiromycin, prednimustine, puromycin; ranimustine, ristocetins such as ristocetin A; temozolamide; teniposide; tomudex; topotecan; tubercidin, ubenimax, valrubicin (N-trifluoroacetyladriamycin-14-valerate), vinorelbine, vinblastine, vindesine, vinorelbine, and zorubicin and analogs, derivatives, pharmaceutically acceptable salts, esters, prodrugs, codrugs, and protected forms thereof.

Suitable antibacterial compounds include capreomycins, including capreomycin IA, capreomycin IB, capreomycin IIA and capreomycin IIB; carbomycins, including carbomycin A; carumonam; cefaclor, cefadroxil, cefamandole, cefatrizine, cefazedone, cefazolin, cefbuperazone, cefcapene pivoxil, cefclidin, cefdinir, cefditoren, cefime, ceftamet, cefmenoxime, cefinetzole, cefininox, cefodizime, cefonicid, cefoperazone, ceforanide, cefotaxime, cefotetan, cefotiam, cefoxitin, cefpimizole, cefpiramide, cefpirome, cefprozil, cefroxadine, cefsulodin, ceftazidime, cefteram, ceftezole, ceftibuten, ceftiofur, ceftizoxime, ceftriaxone, cefuroxime, cefuzonam, cephalexin, cephalogycin, cephaloridine, cephalosporin C, cephalothin, cephapirin, cephamycins, such as cephamycin C, cephradine, chlortetracycline; chlarithromycin, clindamycin, clometocillin, clomocycline, cloxacillin, cyclacillin, danofloxacin, demeclocyclin, destomycin A, dicloxacillin, dicloxacillin, dirithromycin, doxycyclin, epicillin, erythromycin A, ethanbutol, fenbenicillin, flomoxef, florfenicol, floxacillin, flumequine, fortimicin A, fortimicin B, forfomycin, foraltadone, fusidic acid, gentamycin, glyconiazide, guamecycline, hetacillin, idarubicin, imipenem, isepamicin, josamycin, kanamycin, leumycins such as leumycin $A_1$, lincomycin, lomefloxacin, loracarbef, lymecycline, meropenam, metampicillin, methacycline, methicillin, mezlocillin, micronaomicin, midecamycins such as midecamycin $A_1$, mikamycin, minocycline, mitomycins such as mitomycin C, moxalactam, mupirocin, nafcillin, netilicin, norcardians such as norcardian A, oleandomycin, oxytetracycline, panipenam, pazufloxacin, penamecillin, penicillins such as penicillin G, penicillin N and penicillin O, penillic acid, pentylpenicillin, peplomycin, phenethicillin, pipacyclin, piperacilin, pirlimycin, pivampicillin, pivcefalexin, porfiromycin, propiallin, quinacillin, ribostamycin, rifabutin, rifamide, rifampin, rifamycin SV, rifapentine, rifaximin, ritipenem, rekitamycin, rolitetracycline, rosaramicin, roxithromycin, sancycline, sisomicin, sparfloxacin, spectinomycin, streptozocin, sulbenicillin, sultamicillin, talampicillin, teicoplanin, temocillin, tetracyclin, thostrepton, tiamulin, ticarcillin, tigemonam, tilmicosin, tobramycin, tropospectromycin, trovafloxacin, tylosin, and vancomycin, and analogs, derivatives, pharmaceutically acceptable salts, esters, prodrugs, codrugs, and protected forms thereof.

Antiproliferative/antimitotic drugs and prodrugs include natural products such as vinca alkaloids (e.g., vinblastine, vincristine, and vinorelbine), paclitaxel, epidipodophyllotoxins (e.g., etoposide, teniposide), antibiotics (e.g., actinomycins, daunorubicin, doxorubicin and idarubicin), anthracyclines, mitoxantrone, bleomycins, plicamycin (mithramycin) and mitomycin, enzymes (e.g., L-asparaginase); antiplatelet prodrugs; antiproliferative/antimitotic alkylating prodrugs such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes, dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine); platinum coordination complexes (cisplatin, carboplatin), procarbazine, hydroxyurea, mitotane, aminoglutethimide; hormones (e.g., estrogen, progestin); anticoagulants (e.g., heparin, synthetic heparin salts and other inhibitors of thrombin); fibrinolytic prodrugs such as tissue plasminogen activator, streptokinase and urokinase, aspirin, dipyridamole, ticlopidine, clopidogrel, abciximab; antimigratory; antisecretory (breveldin); anti-inflammatory agents such as corticosteroids (cortisol, cortisone, fludrocortisone, flucinolone, prednisone, prednisolone, methylprednisolone, triamcinolone, betamethasone, and dexamethasone), NSAIDS (salicylic acid and derivatives, aspirin, acetaminophen, indole and indene acetic acids (indomethacin, sulindac and etodalac), heteroaryl acetic acids (tolmetin, diclofenac, and ketorolac), arylpropionic acids (e.g., ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (e.g., cyclosporine, tacrolimus (FK-506), sirolimus (rapamycin), azathioprine, and mycophenolate mofetil); angiogenic agents such as vascular endothelial growth factor (VEGF), fibroblast growth factor (FGF); angiotensin receptor blocker; nitric oxide donors; anti-sense oligonucleotides and combinations thereof; cell cycle inhibitors, mTOR inhibitors, growth factor signal transduction kinase inhibitors, neovascularization inhibitors, angiogenesis inhibitors, and apoptosis inhibitors, and analogs, derivatives, pharmaceutically acceptable salts, esters, prodrugs, codrugs, and protected forms thereof.

The systems described herein may be usefully employed in the administration of antiviral agents. Thus, in one aspect, there is disclosed herein a method for treating or reducing the risk of retroviral or lentiviral infection comprising injecting a sustained release drug delivery system including an antiviral agent in a patient in need of treatment wherein a dose of said agent is released for at least 7 days. Another aspect of the system provides a method for treating or reducing the risk of retroviral or lentiviral infection comprising injecting a sustained release drug delivery system including an antiviral agent in a patient in need of treatment wherein release of said agent maintains a desired concentration of said agent in blood plasma for at least 7 days.

In certain embodiments, the system reduces the risk of mother to child transmission of viral infections. Examples of viral infections include HIV, Bowenoid Papulosis, Chickenpox, Childhood HIV Disease, Human Cowpox, Hepatitis C, Dengue, Enteroviral, Epidermodysplasia Verruciformis, Erythema Infectiosum (Fifth Disease), Giant Condylomata Acuminata of Buschke and Lowenstein, Hand-Foot-and-Mouth Disease, Herpes Simplex, Herpes Virus 6, Herpes Zoster, Kaposi Varicelliform Eruption, Rubeola Measles, Milker's Nodules, Molluscum Contagiosum, Monkeypox, Orf, Roseola Infantum, Rubella, Smallpox, Viral Hemorrhagic Fevers, Genital Warts, and Nongenital Warts.

In some embodiments, the antiviral agent is selected from azidouridine, anasmycin, amantadine, bromovinyldeoxusidine, chlorovinyldeoxusidine, cytarbine, didanosine, deoxynojirimycin, dideoxycitidine, dideoxyinosine, dideoxynucleoside, desciclovir, deoxyacyclovir, edoxuidine, enviroxime, fiacitabine, foscamet, fialuridine, fluorothymidine, floxuridine, hypericin, interferon, interleukin, isethionate, nevirapine, pentamidine, ribavirin, rimantadine, stavirdine, sargramostin, suramin, trichosanthin, tribromothymidine, trichlorothymidine, vidarabine, zidoviridine, zalcitabine and 3-azido-3-deoxythymidine. In certain embodiments, the antiviral agent is selected from nevirapine, delavirdine and efavirenz. In preferred embodiments, the antiviral agent is nevirapine.

In other embodiments, the antiviral agent is selected from 2',3'-dideoxyadenosine (ddA), 2',3'-dideoxyguanosine (ddG), 2',3'-dideoxycytidine (ddC), 2',3'-dideoxythymidine (ddT), 2',3'-dideoxy-dideoxythymidine(d4T), 2'-deoxy-3'-thia-cytosine (3TC or lamivudime), 2',3'-dideoxy-2'-fluoroadenosine, 2',3'-dideoxy-2'-fluoroinosine, 2',3'-dideoxy-2'-fluorothymidine, 2',3'-dideoxy-2'-fluorocytosine, 2'3'-dideoxy-2',3'-didehydro-2'-fluorothymidine (Fd4T), 2'3'-dideoxy-2'-beta-fluoroadenosine (F-ddA), 2'3'-dideoxy-2'-beta-fluoro-inosine (F-ddI), and 2',3'-dideoxy-2'-beta-flurocytosine (F-ddC).

In some embodiments, the antiviral agent is selected from trisodium phosphomonoformate, ganciclovir, trifluorothymidine, acyclovir, 3'azido-3'thymidine (AZT), dideoxyinosine (ddI), idoxuridine.

Exemplary antiviral drug include selected from the group consisting of acyclovir, azidouridine, anasmycin, amantadine, bromovinyldeoxusidine, chlorovinyldeoxusidine, cytarbine, didanosine, deoxynojirimycin, dideoxycitidine, dideoxyinosine, dideoxynucleoside, desciclovir, deoxyacyclovir, edoxuidine, enviroxime, fiacitabine, foscamet, fialuridine, fluorothymidine, floxuridine, ganciclovir, hypericin, interferon, interleukin, isethionate, idoxuridine, nevirapine, pentamidine, ribavirin, rimantadine, stavirdine, sargramostin, suramin, trichosanthin, trifluorothymidine, tribromothymidine, trichlorothymidine, trisodium phosphomonoformate, vidarabine, zidoviridine, zalcitabine and 3-azido-3-deoxythymidine.

In certain embodiments, the antiviral agent is one which inhibits or reduces HIV infection or susceptibility to HIV infection. Non-nucleoside analogs are preferred and include compounds, such as nevirapine, delavirdine and efavirenz, to name a few. However, nucleoside derivatives, although less preferable, can also be used, including compounds such as 3'azido-3'thymidine (AZT), dideoxyinosine (ddI), 2',3'-dideoxyadenosine (ddA), 2',3'-dideoxyguanosine (ddG), 2',3'-dideoxycytidine (ddC), 2',3'-dideoxythymidine (ddT), 2'3'-dideoxy-dideoxythymidine (d4T), and 2'-deoxy-3'-thiacytosine (3TC or lamivudime). Halogenated nucleoside derivatives may also be used including, for example, 2'3'-dideoxy-2'-fluoronucleosides such as 2',3'-dideoxy-2'-fluoroadenosine, 2',3'-dideoxy-2'-fluoroinosine, 2',3'-dideoxy-2-fluorothymidine, 2',3'-dideoxy-2'-fluorocytosine, and 2',3'-dideoxy-2',3'-didehydro-2'-fluoronucleosides including, but not limited to2'3'-dideoxy-2',3'-didehydro-2'-fluorothymidine (Fd4T), 2'3-dideoxy-2'-beta-fluoroadenosine (F-ddA), 2'2'-dideoxy-2'-beta-fluoro-inosine (F-ddI) and 2',3'-dideoxy-2'-beta-flurocytosine (F-ddC).

Any pharmaceutically acceptable form of such a compound may be employed in the practice of the present invention, i.e., the free base or a pharmaceutically acceptable salt or ester thereof. Pharmaceutically acceptable salts, for instance, include sulfate, lactate, acetate, stearate, hydrochloride, tartrate, maleate, and the like.

The phrase "pharmaceutically acceptable carrier" as used herein means a pharmaceutically acceptable material, composition or vehicle, such as a liquid or solid filler, diluent, excipient, or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; and (16) other non-toxic compatible substances employed in pharmaceutical formulations.

Codrugs or prodrugs may be used to deliver drugs in a sustained manner. In certain embodiments, codrugs and prodrugs may be adapted to use in the core 116 or skin 114 of the drug delivery devices described above. An example of sustained-release systems using codrugs and prodrugs may be found in U.S. Pat. No. 6,051,576. This reference is incorporated in its entirety herein by reference. In other embodiments, codrugs and prodrugs may be included with the gelling, suspension, and other embodiments described herein.

As used herein, the term "codrug" means a first constituent moiety chemically linked to at least one other constituent moiety that is the same as, or different from, the first constituent moiety. The individual constituent moieties are reconstituted as the pharmaceutically active forms of the same moieties, or codrugs thereof, prior to conjugation. Constituent moieties may be linked together via reversible covalent bonds such as ester, amide, carbamate, carbonate, cyclic ketal, thioester, thioamide, thiocarbamate, thiocarbonate, xanthate and phosphate ester bonds, so that at the required site in the body they are cleaved to regenerate the active forms of the drug compounds.

As used herein, the term "constituent moiety" means one of two or more pharmaceutically active moieties so linked as to form a codrug according to the present invention as described herein. In some embodiments according to the present invention, two molecules of the same constituent moiety are combined to form a dimer (which may or may not have a plane of symmetry). In the context where the free, unconjugated form of the moiety is referred to, the term "constituent moiety" means a pharmaceutically active moiety, either before it is combined with another pharmaceutically active moiety to form a codrug, or after the codrug has been hydrolyzed to remove the linkage between the two or more constituent moieties. In such cases, the constituent moieties are chemically the same as the pharmaceutically active forms of the same moieties, or codrugs thereof, prior to conjugation.

The term "prodrug" is intended to encompass compounds that, under physiological conditions, are converted into the therapeutically active agents of the present invention. A common method for making a prodrug is to include selected moieties, such as esters, that are hydrolyzed under physiological conditions to convert the prodrug to an active biological moiety. In other embodiments, the prodrug is converted by an enzymatic activity of the host animal. Prodrugs are typically formed by chemical modification of a biologically active moiety. Conventional procedures for the selection and preparation of suitable prodrug derivatives are described, for example, in Design of Prodrugs, ed. H. Bundgaard, Elsevier, 1985.

In the context of referring to the codrug according to the present invention, the term "residue of a constituent moiety" means that part of a codrug that is structurally derived from a constituent moiety apart from the functional group through which the moiety is linked to another constituent moiety. For instance, where the functional group is —NH$_2$, and the constituent group forms an amide (—NH—CO—) bond with another constituent moiety, the residue of the constituent moiety is that part of the constituent moiety that includes the —NH— of the amide, but excluding the hydrogen (H) that is lost when the amide bond is formed. In this sense, the term "residue" as used herein is analogous to the sense of the word "residue" as used in peptide and protein chemistry to refer to a residue of an amino acid in a peptide.

Codrugs may be formed from two or more constituent moieties covalently linked together either directly or through a linking group. The covalent bonds between residues include a bonding structure such as:

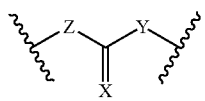

wherein Z is O, N, —CH$_2$—, —CH$_2$—O— or —CH$_2$—S—, Y is O, or N, and X is O or S. The rate of cleavage of the individual constituent moieties can be controlled by the type of bond, the choice of constituent moieties, and/or the physical form of the codrug. The lability of the selected bond type may be enzyme-specific. In some embodiments, the bond is selectively labile in the presence of an esterase. In other embodiments of the invention, the bond is chemically labile, e.g., to acid- or base-catalyzed hydrolysis. In some embodiments, the linking group does not include a sugar, a reduced sugar, a pyrophosphate, or a phosphate group.

The physiologically labile linkage may be any linkage that is labile under conditions approximating those found in physiologic fluids. The linkage may be a direct bond (for instance, ester, amide, carbamate, carbonate, cyclic ketal, thioester, thioamide, thiocarbamate, thiocarbonate, xanthate, phosphate ester, sulfonate, or a sulfamate linkage) or may be a linking group (for instance, a $C_1$-$C_{12}$ dialcohol, a $C_1$-$C_{12}$ hydroxyalkanoic acid, a $C_1$-$C_{12}$ hydroxyalkylamine, a $C_1$-$C_{12}$ diacid, a $C_1$-$C_{12}$ aminoacid, or a $C_1$-$C_{12}$ diamine). Especially preferred linkages are direct amide, ester, carbonate, carbamate, and sulfamate linkages, and linkages via succinic acid, salicylic acid, diglycolic acid, oxa acids, oxamethylene, and halides thereof. The linkages are labile under physiologic conditions, which generally means pH of about 6 to about 8. The lability of the linkages depends upon the particular type of linkage, the precise pH and ionic strength of the physiologic fluid, and the presence or absence of enzymes that tend to catalyze hydrolysis reactions in vivo. In general, lability of the linkage in vivo is measured relative to the stability of the linkage when the codrug has not been solubilized in a physiologic fluid. Thus, while some codrugs may be relatively stable in some physiologic fluids, nonetheless, they are relatively vulnerable to hydrolysis in vivo (or in vitro, when dissolved in physiologic fluids, whether naturally occurring or simulated) as compared to when they are neat or dissolved in non-physiologic fluids (e.g., non-aqueous solvents such as acetone). Thus, the labile linkages are such that, when the codrug is dissolved in an aqueous solution, the reaction is driven to the hydrolysis products, which include the constituent moieties set forth above.

Codrugs for preparation of a drug delivery device for use with the systems described herein may be synthesized in the manner illustrated in one of the synthetic schemes below. In general, where the first and second constituent moieties are to be directly linked, the first moiety is condensed with the second moiety under conditions suitable for forming a linkage that is labile under physiologic conditions. In some cases it is necessary to block some reactive groups on one, the other, or both of the moieties. Where the constituent moieties are to be covalently linked via a linker, such as oxamethylene, succinic acid, or diglycolic acid, it is advantageous to first condense the first constituent moiety with the linker. In some cases it is advantageous to perform the reaction in a suitable solvent, such as acetonitrile, in the presence of suitable catalysts, such as carbodiimides including EDCI (1-ethyl-3-(3-dimethylaminopropyl)-carbodiimide) and DCC (DCC: dicyclohexylcarbo-diimide), or under conditions suitable to drive off water of condensation or other reaction products (e.g., reflux or molecular sieves), or a combination of two or more thereof. After the first constituent moiety is condensed with the linker, the combined first constituent moiety and linker may then be condensed with the second constituent moiety. Again, in some cases it is advantageous to perform the reaction in a suitable solvent, such as acetonitrile, in the presence of suitable catalysts, such as carbodiimides including EDCI and DCC, or under conditions suitable to drive off water of condensation or other reaction products (e.g., reflux or molecular sieves), or a combination of two or more thereof. Where one or more active groups have been blocked, it may be advantageous to remove the blocking groups under selective conditions, however it may also be advantageous, where the hydrolysis product of the blocking group and the blocked group is physiologically benign, to leave the active groups blocked.

The person having skill in the art will recognize that, while diacids, dialcohols, amino acids, etc., are described as being suitable linkers, other linkers are contemplated as being within the present invention. For instance, while the hydrolysis product of a codrug described herein may comprise a diacid, the actual reagent used to make the linkage may be, for example, an acylhalide such as succinyl chloride. The person having skill in the art will recognize that other possible acid, alcohol, amino, sulfato, and sulfamoyl derivatives may be used as reagents to make the corresponding linkage.

Where the first and second constituent moieties are to be directly linked via a covalent bond, essentially the same process is conducted, except that in this case there is no need for a step of adding a linker. The first and second constituent moieties are merely combined under conditions suitable for forming the covalent bond. In some cases it may be desirable to block certain active groups on one, the other, or both of the constituent moieties. In some cases it may be desirable to use a suitable solvent, such as acetonitrile, a catalyst suitable to form the direct bond, such as carbodiimides including EDCI and DCC, or conditions designed to drive off water of condensation (e.g., reflux) or other reaction by-products.

While in some cases the first and second moieties may be directly linked in their original form, it is possible for the active groups to be derivatized to increase their reactivity. For instance, where the first moiety is an acid and the second moiety is an alcohol (i.e., has a free hydroxyl group), the first moiety may be derivatized to form the corresponding acid halide, such as an acid chloride or an acid bromide. The person having skill in the art will recognize that other possibilities exist for increasing yield, lowering production costs, improving purity, etc., of the codrug described herein by using conventionally derivatized starting materials to make the codrugs described herein.

The first and second constituent moieties of the codrug may be any drug, including any of the agents listed above, and analogs, derivatives, pharmaceutically acceptable salts, esters, prodrugs, codrugs, and protected forms thereof. In certain embodiments, the first and second constituent moieties are different drugs; in other embodiments, they are the same.

In certain codrug embodiments, the first constituent moiety is an NSAID. In some embodiments, the second constituent moiety is corticosteroid. In certain embodiments, the first constituent moiety is 5-FU)and the second is TA. In certain embodiments, the first constituent moiety is a beta lactam antibiotic such as amoxicillin and the second is a beta lactamase inhibitor such as clavulanate.

Exemplary reaction schemes according to the present invention are illustrated in Schemes 1-4, below. These Schemes can be generalized by substituting other therapeutic agents having at least one functional group that can form a covalent bond to another therapeutic agent having a similar or different functional group, either directly or indirectly through a pharmaceutically acceptable linker. The person of skill in the art will appreciate that these schemes also may be generalized by using other appropriate linkers.

SCHEME 1

wherein L is an ester linker —COO—, and $R_1$ and $R_2$ are the residues of the first and second constituent moieties or pharmacological moieties, respectively.

SCHEME 2

wherein L is the amide linker —CONH—, and $R_1$ and $R_2$ have the meanings given above.

SCHEME 3

Step 1:

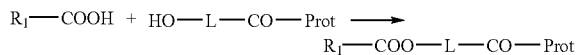

wherein Prot is a suitable reversible protecting group.
Step 2: $R_1$—COO-L-CO-Prot→$R_1$—COO-L-COOH
Step 3: $R_1$—COO-L-COOH+$R_2$—OH→$R_1$—COO-L-COOR$_2$
wherein $R_1$, L, and $R_2$ have the meanings set forth above.

SCHEME 4

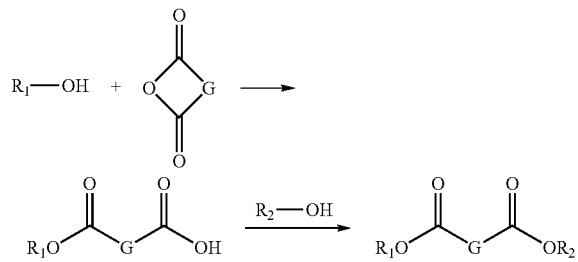

wherein $R_1$ and $R_2$ have the meanings set forth above and G is a direct bond, an $C_1$-$C_4$ alkylene, a $C_2$-$C_4$ alkenylene, a $C_2$-$C_4$ alkynylene, or a 1,2-fused ring, and G together with the anhydride group completes a cyclic anhydride. Suitable anhydrides include succinic anhydride, glutaric anhydride, maleic anhydride, diglycolic anhydride, and phthalic anhydride.

As noted above, drugs may also be included in material 122, and therefore incorporated in the skin 114 of an extruded product segment 112$_f$. This may provide biphasic release with an initial burst such that when such a system is first placed in the body, a substantial fraction of the total drug released is released from the skin 114. Subsequently, more drug is released from the core 116. The drug(s) included in the skin 114 may be the same drug(s) as inside the core 116. Alternatively, the drugs included in the skin 114 may be different from the drug(s) included in the core 116. For example, the core 116 may include 5-FU while the skin 114 may include TA or loteprednol etabonate.

As noted in certain examples above, it will be appreciated that a variety of materials may be used for the skin 114 to achieve different release rate profiles. For example, as discussed in the aforementioned '972 patent, an outer layer (such as the skin 114) may be surrounded by an additional layer that is permeable, semi-permeable, or impermeable (element numbers 110, 210, and 310 in the '972 patent), or may itself be formed of a permeable or semi-permeable material. Accordingly, co-extruded devices may be provided with one or more layers using techniques and materials fully described in the '972 patent. These additional layers may be provided, for example with a third, concentric co-extruded material from a co-extrusion device that can co-extrude three materials at one time. Through such permeable or semi-permeable materials, active agents in the core may be released at various controlled rates. In addition, even materials considered to be impermeable may permit release of drugs or other active agents in the core 116 under certain circumstances. Thus, permeability of the skin 114 may contribute to the release rate of an active agent over time, and may be used as a parameter to control the release rate over time for a deployed device.

Further, a continuous mass of co-extruded product 112 may be segmented into devices 112$_f$ having, for example, an impermeable skin 114 surrounding a core 116, with each segment further coated by a semi-permeable or permeable layer to control a release rate through the exposed ends thereof. Similarly, the skin 114, or one or more layers thereof, or a layer surrounding the device, may be bioerodible at a known rate, so that core material is exposed after a certain period of time along some or all of the length of the tube, or at one or both ends thereof.

Thus, it will be appreciated that, using various materials for the skin 114 and one or more additional layers surrounding a co-extruded device, the delivery rate for the deployed device may be controlled to achieve a variety of release rate profiles.

Extrusion, and more particularly co-extrusion, of the product 112 permits very close tolerances of the dimensions of the product. It has been found that a significant factor affecting the release rate of drug from a device formed from the product 112 is the internal diameter of the skin 114, which relates to the (at least initial) total surface area available for drug diffusion. Thus, by maintaining close tolerances of the inner diameter of the skin 114, the variation in release rates from the drug cores of batches of devices can be reduced. The outside diameter of the delivery device may also be controlled by varying the processing parameters, such as the conveyor speed and the die diameter.

EXAMPLE

A co-extrusion line consisting of two Randcastle microtruders, a concentric co-extrusion die, and a conveyer may be used to manufacture an injectable delivery device for FA. Micronized powder of FA may be granulated with the following matrix-forming material: PCL or poly(vinyl acetate) (PVAC) at a drug loading level of 40% or 60%. The resulting mixture may be co-extruded with or without PLGA or EVA as an outer layer coating to form a composite tube-shaped product. In-vitro release studies may be carried out using pH 7.4 phosphate buffer to evaluate the release characteristics of FA from different delivery devices.

FA granules used to form the drug core may be prepared by mixing 100 g of FA powder with 375 g and 167 g of 40% PCL solution to prepare 40% and 60% drug loading formulations, respectively. After oven-drying at 55° C. for 2 hours, the granules may be ground to a size 20 mesh manually or using a cryogenic mill. The resulting drug/polymer mixture may be used as material 124 and co-extruded with PLGA as material 122 using two Randcastle Model RCP-0250 microextruders to form a composite co-extruded, tube-shaped product 112.

Preparations as described in the Example above were capable of providing long-term sustained release of FA, as depicted in FIGS. 2-5. As may be seen from the Figures, the release of FA from a PCL matrix without the outer layer of polymeric coat was much faster than that with PLGA skin. It showed a bi-phase release pattern: a burst release phase followed by a slow release phase. On the other hand, the preparation with the PLGA coat gave a linear release of FA for at least five months regardless of the drug level. The PLGA coating appeared to be able to minimize the burst effect significantly. It also was observed that the release rate of FA was proportional to the drug loading level in the matrix. Compared to PLGA, EVA largely retarded the release of FA. In addition to variations in release rate, it will be appreciated that different polymers may possess different physical properties for extrusion.

In co-extruded injectable drug delivery devices, the release of drugs, such as steroids, can be attenuated by using a different combination of inner matrix-forming materials and outer polymeric materials. This makes these devices suitable for a variety of applications where controlled and sustained release of drugs, including steroids, is desired. As described below, simple extrusion, i.e., extrusion of a single material or mixture, may also be used to extrude a skin which is then cured and filled with a drug core mixture in a non-extrusion process.

Figure 6:
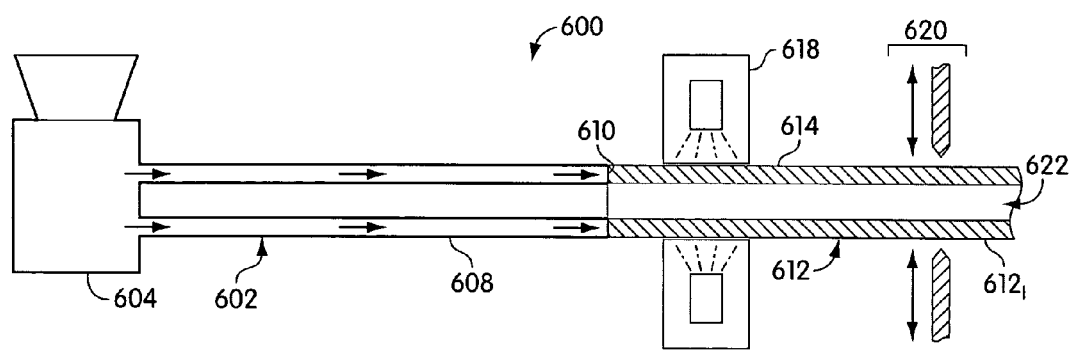
FIG. 6 shows an apparatus for extruding a skin for a drug delivery device.

FIG. 6 shows an apparatus for extruding a skin for a drug delivery device. As illustrated, a system 600 may include an extrusion device 602 having an extruder 604 connected to a die head 608 in a manner well known to those of skill in the extrusion arts. The die head 608 may have an exit port 610 out of which materials from the extruder 604 are forced. The die head 608 and/or exit port 610 may establish a cross-sectional shape of extruded matter. Commercially available extruders may be used as the extruder 604, including the Randcastle model RCP-0250 Microtruder (Randcastle Extrusion Systems, Cedar Grove, N.J.), and its associated heaters, controllers, and the like. Exemplary extruders are also disclosed, for example, in U.S. Pat. Nos. 5,569,429, 5,518,672, and 5,486,328. In general, the system 600 may be a system as described above with reference to FIG. 1, except that no central core is co-extruded with the skin 614, leaving an open center region 622.

A curing station 618 and a segmenting station 620 may also be provided, and may be as described above with reference to FIG. 1. It will be appreciated that the center region 622 may have a tendency to collapse under gravity. In one embodiment, the extruded material 612 may be extruded vertically so that it may be cured and/or segmented without gravity collapsing the walls of the skin 614, resulting in undesired adhesion and closure of the center region 622. The extruded material 612 may be segmented at the segmenting station 620 into a plurality of segments 612$_f$ that may form a skin for a sustained release drug delivery device.

It will be appreciated that other techniques may be employed to preform a tube or straw useful for making the injectable drug delivery devices described herein. One technique that has been successfully employed is to dip a wire, such as Nitinol, of suitable outside diameter into an uncured polyimide or other suitable polymer. The polyimide then may be cured. The wire may then be withdrawn from the polyimide to provide a polymer tube into which desired drug formulations may be injected or otherwise inserted. This technique has been used, for example, to construct the devices characterized in FIG. 10 below.

Similarly, injectable devices may be constructed using preformed cores of drug or drug matrix material. The core may be formed by extrusion, compression, or other means and then sprayed or otherwise coated with a film of material having suitable properties. The core, whether prepared in segments or a continuous length of material that will be cut into segments, may be dip coated in an uncured polymer or other suitable material and, if appropriate, may be cured to form drug delivery devices of suitable dimensions.

The outer polymer layer, however formed, may be permeable, non-permeable, or partially permeable according to the type of core and the desired release rate profile for the device. The outer layer may also include one or more pores that provide a means for ingress of biological fluids or water and egress of active agents from the core. The outer layer may also be bioerodible or non-bioerodible. Bioerodible outer layers may erode at a rate that is faster or slower than (or the same as) an erosion rate of the core, which may itself be bioerodible or non-bioerodible. Suitable materials for the outer layer include any biocompatible polymer, including, but not limited to, PCL, EVA, PEG, PVA, PLA, PGA, PLGA, polyimide, polyalkyl cyanoacrylate, polyurethane, nylons, or copolymers thereof. In polymers including lactic acid monomers, the lactic acid may be D-, L-, or any mixture of D-and L-isomers. All such outer layers may be suitably employed with any of the injectable devices described herein.

In certain embodiments, the core may be fashioned of a drug matrix that independently controls release rate of one or more drugs within the core, using, for example, the extrusion or compression techniques noted above. In such embodiments, the outer polymer layer may be omitted entirely, or the core may be coated with a layer that affects other properties of the injectable device, including lubricants or adhesives.

Figure 7:
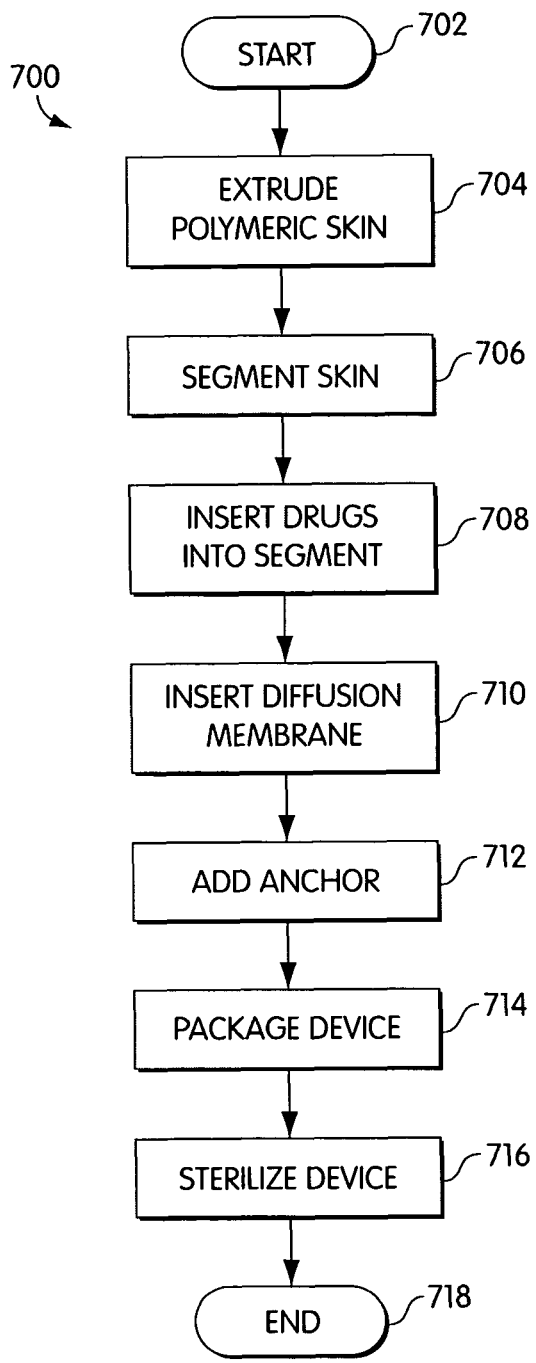
FIG. 7 is a flow chart of a process for making an injectable drug delivery device.

FIG. 7 is a flow chart of a process for making an injectable drug delivery device. The method 700 may begin by extruding a polymeric skin 704 using an extruder such as the extruder described above with reference to FIG. 6. Any suitable polymer may be used, including a bioerodible polymer or a polymer with a desired permeability, such as impermeability, semi-permeability, or permeability to either a drug to be delivered or a biological fluid in which the device is to be placed. Erodability and permeability may be selected according to a desired drug (and the solubility thereof), a desired release rate, and an expected biological environment, as discussed generally above. One suitable polymer for intraocular and periocular applications is polyimide.

The continuous mass of extruded skin may be segmented, as shown in step 706, into individual segments having an open central region. Segmenting may be performed, for example, using the segmenting station described in reference to FIGS. 1 & 6 above.

As shown in step 708, drugs may be inserted into a segment cut from the mass of extruded skin. The drug may be any of the drugs and drug formulations described above, and may include release-rate controlling formulations such as biocompatible gels, admixtures, polymer/drug matrices, granulated drug compounds, or any other formulations suitable for inserting by injection or other techniques into the segment. One suitable formulation is a slurry of PVA and FA that may be forced into the segment and cured.

As shown in step 710, a diffusion membrane may be provided to limit the release rate of the drug core. The diffusion membrane may operate by, for example, limiting fluid flow into the drug core or limiting the passage of drugs out of the drug core. Additional processing steps may be performed. For example, the cured and drug-loaded segment in step 708 may be inserted into an additional polymer tube, such as polyimide, of slightly wider and longer dimensions. This additional tube may provide a reservoir on one or both ends, which may be filled with, for example, the diffusion membrane on one or both ends of the device.

As shown in step 712, an anchor may be attached to the device. As used herein, the term "anchor" is intended to refer to anything used to secure the device in a location within a body, such as a small eye for receiving a suture, an expanding wire or flexible material that clasps the puncture hole formed by the needle that injects the device, an adhesive, or the like. Any mechanism suitable for securing the device in its intended location and suitable for use with an injectable drug delivery device may be used as an anchor. In one embodiment, a reservoir, such as the reservoir described above with reference to step 710, may be filled with a curable adhesive, such as an ultraviolet curable adhesive. A portion of an anchor may be inserted into the adhesive, and the adhesive may be cured, such as by applying ultraviolet radiation, so that the anchor is secured to the device.

As shown in step 714, the device may be packaged, such as by preloading a needle of appropriate gauge with the device and enclosing the assembly in a suitable package for shipment to an end user. As shown in step 716, the closed package may further be sterilized in any suitable manner.

It will be appreciated that in various embodiments, certain of the above steps may be omitted, altered, or rearranged, provided that the steps utilized result in an injectable, sustained release drug delivery device. For example, the step of adding a diffusion membrane 710 may be omitted entirely, or may be replaced by a step of coating the entire device with a polymer coating of suitable properties. In another embodiment, a length of extruded polymeric skin may be filled with a drug core, after which the entire mass may be cured (if appropriate) and cut into a number of segments. It should also be understood that certain steps, such as curing the extruded skin, may be adapted to a particular manufacturing method, such as by partially curing the skin at one step, with additional curing occurring at a subsequent processing step. All such variations are intended to fall within the scope of this description, provided that they result in an injectable, sustained-release drug delivery device as described herein.

Figure 8:
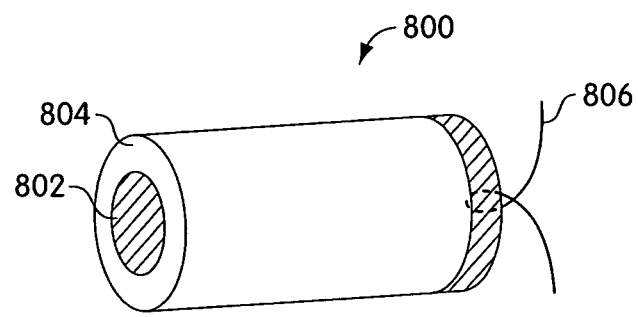
FIG. 8 shows an injectable drug delivery device.

FIG. 8 shows an injectable drug delivery device. The device 800 may include a drug core 802, a skin 804 of one or more polymer layers, and an anchor 806 attached to the device 800. The drug core 802, the skin 804, and the anchor 806 may be any of the cores, skins, and anchors described herein. In certain configurations, the release rate may be determined primarily by the surface area of the core 802 at an end of the device 800, and a duration of release may be determined primarily by a length of the device 800.

It will further be appreciated that an injectable drug delivery device of suitable size and drug release characteristics may be fashioned in other ways. For example, a solid, compressed device formed of a drug/polymer matrix may have suitable release properties for use without a skin 804 or other coating that affects release rate. The compressed device may be formed, for example, as a cylindrical mass that is extruded using the extruder of FIG. 6, and then cured into a solid mass (before or after segmenting). The compressed device may instead be formed by compressing granules of drug, either alone or in mixture with other substances, into a preformed mold of suitable size.

It will be appreciated that a significant advantage of many of the methods of making an injectable device as described above is that stability of the drug itself may be controlled and/or improved. For example, when contained in the core, the drug may be protected from forces in the external environment that may degrade or alter its activity, whether in manufacturing, in storage, or in use. The matrix in the drug core and/or the skin layer(s) may provide a measure of protection. Thus, for example, where a device includes a drug core, an inner skin and an outer skin, the inner skin may be composed of ultraviolet absorbable material (e.g., polyimide). If the outer layer is cured during fabrication using ultraviolet light, the inner skin may prevent the ultraviolet irradiation from coming into contact with the drug in the core. Thus, the drug is less likely to degrade during the curing process. The skin(s) and core matrix may also protect the drug from chemical degradation and metabolism in biological fluids by controlling and limiting the interaction of the drug and fluid. This mechanism may also aid in stabilizing the drug in the device during storage by limiting the interaction of the drug with air or humidity.

Figure 9:
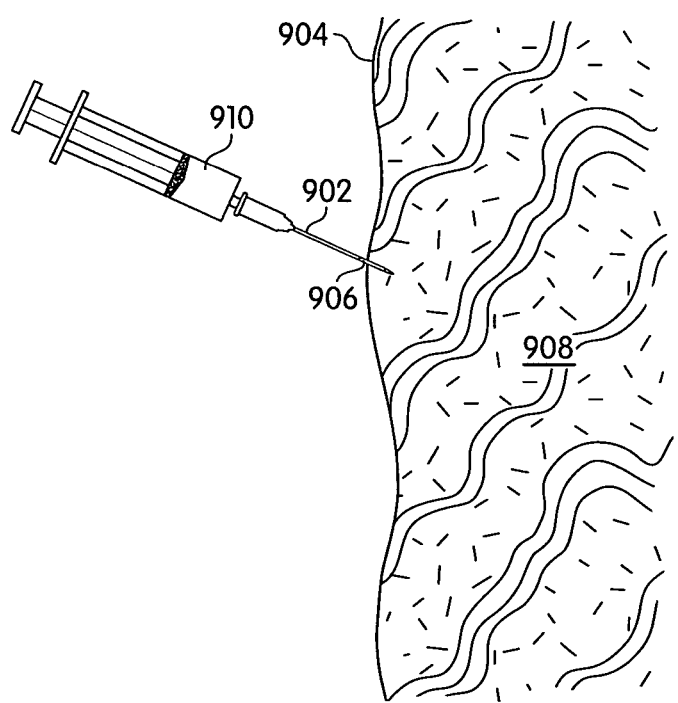
FIG. 9 shows an injectable drug delivery system.

FIG. 9 shows an injectable drug delivery system. In use, a needle 902 may puncture a wall of biological material 904. The needle 902 may be pre-loaded with an injectable drug delivery device 906, which may be injected into a biological medium 908, such as biological fluid or tissue, on an opposing side of the wall 904, and driven into the biological medium 908 by a fluid 910, such as saline, in a reservoir of the needle. Depending on whether an anchor is included in the device 906, and whether the anchor is intended to attach to the biological wall 904, the needle may be variously positioned at different depths within the biological medium 908.

Figure 10:
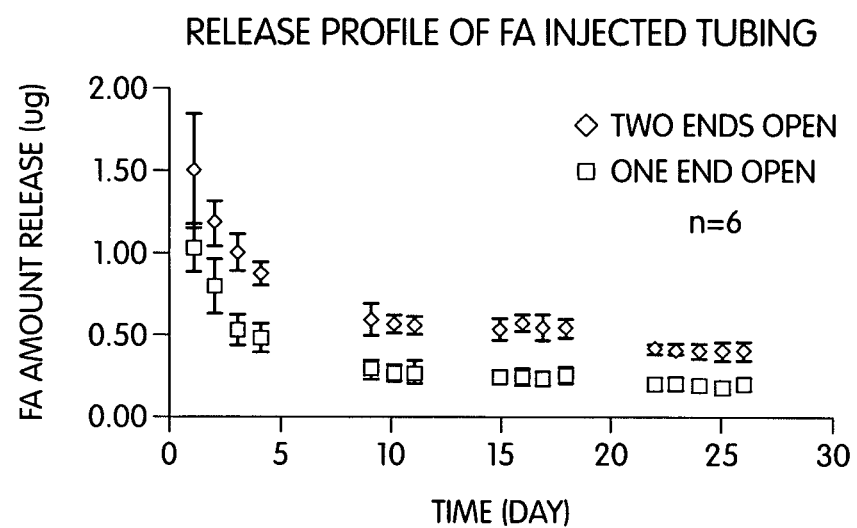
FIG. 10 shows release rates of certain devices.

FIG. 10 shows release rates of certain devices. To test delivery rates, preformed tubes of polyimide with an inner diameter of 0.0115 inches and an outer diameter of 0.0125 inches were prepared using the dipped-wire method described above. Drug delivery devices were then formed by injecting a paste of FA/PVA (in a ratio of 90:10) into the preformed tube. The filled tube was then cut into sections of 3 mm and dried at ambient conditions, after which the sections were cured at 135° C. for two hours. This achieved a total drug loading of about 26 µg/mm in each device. Some of the devices were left with two open ends. Other devices were sealed on one end using a silicone adhesive. As seen in FIG. 10, the devices with two open ends released drug at approximately 0.4 µg/day (after an initial burst of greater release), and the devices with one open end released drug at approximately 0.2 µg/day (also after an initial burst).

While the invention has been described in detail with reference to preferred embodiments thereof, it will be apparent to one skilled in the art that various changes can be made, and equivalents employed, without departing from the scope of the invention. Thus, the invention set forth in the following claims is to be interpreted in the broadest sense allowable by law. Each of the aforementioned references and published documents is incorporated by reference herein in its entirety.

The invention claimed is:

1. A cylindrical drug delivery device shaped and sized for injection through a needle or cannula having a size from about 30 gauge to 23 gauge comprising:
   a core including an effective amount of fluocinolone acetonide, wherein the core comprises a matrix of fluocinolone acetonide particles and one or more polymers;
   a polymeric tube, impermeable to fluocinolone acetonide, longitudinally surrounding the core, the tube comprising polyimide;
   at least one diffusion membrane, permeable or semi-permeable to the passage of fluocinolone acetonide, disposed at an end of the delivery device.

2. The device of claim 1 wherein at least one of the one or more polymers of the core is bioerodible.

3. The device of claim 1 wherein at least one of the one or more polymers of the core is bioerodible.

4. The device of claim 1 wherein at least one of the one or more polymers of the core is radiation curable.

5. The device of claim 1 wherein at least one of the one or more polymers of the core is heat curable.

6. The device of claim 1 wherein at least one of the one or more polymers of the core is evaporation curable.

7. The device of claim 1 wherein at least one of the one or more polymers of the core is curable by catalysis.

8. The device of claim 1 wherein the diffusion membrane further comprises at least one drug.

9. The device of claim 1 further comprising an anchor.

10. The device of claim 1 wherein the device is shaped and sized for at least one of periocular or intraocular injection.

11. The device of claim 1 further comprising an anchor for securing the device after injection.

12. The device of claim 1 wherein the device provides sustained release of fluocinolone acetonide when exposed to a biological medium.

13. The device of claim 1 wherein the core is completely covered by a combination of the polymeric tube and the diffusion membrane.

14. The device of claim 1 wherein the diffusion membrane is bioerodible.

15. The device of claim 14 wherein a release rate of fluocinolone acetonide is influenced by an erosion of the second polymeric skin.

16. The device of claim 14 wherein a release rate fluocinolone acetonide is independent of an erosion of the diffusion membrane.

17. The device of claim 13 wherein each of the core and the diffusion membrane is bioerodible.

18. The device of claim 13 wherein a release rate of fluocinolone acetonide is controlled by at least one of the permeability of the diffusion membrane to the at least one of the one or more drugs and a surface area of the core that is not covered by the polymeric tube.

19. The device of claim 13 wherein at least one of the polymeric tube and the diffusion membrane prevents direct interaction of biological fluids with the core.

20. The device of claim 13 wherein a release rate of fluocinolone acetonide is controlled by a surface area of the core.

21. The device of claim 13 wherein diffusion of fluocinolone acetonide through the core is not a rate-limiting step of release for the fluocinolone acetonide.

22. The device of claim 13 wherein diffusion of fluocinolone acetonide through the core is a rate-limiting step of release for the fluocinolone acetonide.

23. The device of claim 13 wherein dissolution of fluocinolone acetonide within the core is a rate-limiting step of release for the fluocinolone acetonide.

24. The device of claim 13 wherein the fluocinolone acetonide is more stable within the device than in a biological medium.

25. The device of claim 13 wherein the device provides increased stability of the fluocinolone acetonide to a curing process.

26. The device of claim 13 wherein the device provides increased stability of the fluocinolone acetonide to storage.

27. The device of claim 13 further comprising an anchor.

28. The device of claim 1 wherein the one or more polymers of the core comprise polyvinyl alcohol.

29. The device of claim 1 wherein the diffusion membrane comprises polyvinyl alcohol.

30. The device of claim 1 wherein each end of the device is covered by a diffusion membrane.

31. The device of claim 1 wherein one end of the device is sealed with a silicone adhesive.

* * * * *